US009676620B1

(12) United States Patent
Sokolov et al.

(10) Patent No.: US 9,676,620 B1
(45) Date of Patent: Jun. 13, 2017

(54) SYNTHESIS OF ULTRABRIGHT FLUORESCENT SILICA PARTICLES

(75) Inventors: Igor Sokolov, Potsdam, NY (US); Eun-Bum Cho, Seoul (KR); Dmytro Volkov, Potsdam, NY (US)

(73) Assignee: CLARKSON UNIVERSITY, Potsdam, NY (US)

(*) Notice: Subject to any disclaimer, the term of this patent is extended or adjusted under 35 U.S.C. 154(b) by 994 days.

(21) Appl. No.: 13/044,746

(22) Filed: Mar. 10, 2011

Related U.S. Application Data

(60) Provisional application No. 61/282,644, filed on Mar. 11, 2010, provisional application No. 61/457,086, filed on Dec. 23, 2010.

(51) Int. Cl.
| | |
|---|---|
| *B82Y 40/00* | (2011.01) |
| *B82Y 5/00* | (2011.01) |
| *A61K 8/11* | (2006.01) |
| *A61K 47/02* | (2006.01) |
| *B82Y 30/00* | (2011.01) |
| *A61K 9/51* | (2006.01) |

(52) U.S. Cl.
CPC .................... *B82Y 5/00* (2013.01); *A61K 8/11* (2013.01); *A61K 9/5115* (2013.01); *A61K 47/02* (2013.01); *B82Y 30/00* (2013.01); *B82Y 40/00* (2013.01)

(58) Field of Classification Search
CPC ........... B82Y 25/00; B82Y 5/00; B82Y 40/00; B82Y 30/00; A61K 9/5115; A61K 47/02; A61K 8/11
USPC ........................................................ 427/212
See application file for complete search history.

(56) References Cited

U.S. PATENT DOCUMENTS

| | | | |
|---|---|---|---|
| 5,480,582 A | 1/1996 | Pope | |
| 7,754,646 B2 | 7/2010 | Trau et al. | |
| 8,206,328 B2 | 6/2012 | Adamson | |
| 2003/0124564 A1* | 7/2003 | Trau ...................... | C08G 77/06 435/6.12 |
| 2007/0026407 A1 | 2/2007 | Matsumoto et al. | |
| 2007/0196656 A1* | 8/2007 | Rowell ................. | C09C 1/3081 428/403 |

(Continued)

FOREIGN PATENT DOCUMENTS

| | | |
|---|---|---|
| WO | 2004081222 | 9/2004 |
| WO | 2005023961 | 3/2005 |

(Continued)

OTHER PUBLICATIONS

Naik et al. "Ultrabright Fluorescent Silica Particles: Physical Entrapment of Fluorescent Dye Rhodamine 640 in Nanochannels", Department of Physics and Chemistry, Clarkson University, American Chemical Society, 2008, pp. 214-224.*

(Continued)

*Primary Examiner* — Erma Cameron
(74) *Attorney, Agent, or Firm* — Bond Schoeneck & King, PLLC; Blaine Bettinger; George McGuire

(57) ABSTRACT

The invention generally relates to fluorescent particles and more specifically to silica-based fluorescent nanoporous particles with physically encapsulated organic dyes. In one aspect of the invention, the nanoporous architecture provides a significant enhancement in fluorescence of the particles brightness compared to free dye. A particular chemical control of the silica matrix prevents the dye molecules from leaking the particles.

3 Claims, 18 Drawing Sheets

(56) References Cited

U.S. PATENT DOCUMENTS

| | | | |
|---|---|---|---|
| 2009/0017476 A1* | 1/2009 | Tan | G01N 33/5432 435/7.32 |
| 2012/0187340 A1* | 7/2012 | Sokolov | C01B 33/18 252/301.16 |
| 2014/0051868 A1* | 2/2014 | Sokolov | C09K 11/06 549/214 |

FOREIGN PATENT DOCUMENTS

| | | |
|---|---|---|
| WO | 2006133519 | 12/2006 |
| WO | 2007044711 | 4/2007 |

OTHER PUBLICATIONS

MacCraith et al. "Enhanced Fluorescence Sensing Using Sol-Gel Materials", Journal of Fluorescence, vol. 12. Nos. 3/4, Dec. 2002, pp. 333-342.*
Naik et al. "Synthesis of Mesoporous Silica Fibers and Discoid Endowed with Circular Pore Architecture using Disodium Trioxosilicate as Silica Source", "Microporous and Mesoporous Materials" Elsevier vol. 116, 2008, pp. 581-585.*
Kobler et al. "Colloidal Suspensions of Functionalized Mesoporous Silica Nanoparticles", American Chemical Society, vol. 2, No. 4, 2008, 791-799.*
Blaaderen et al., "Synthesis and Characterization of Colloidal Dispersions of Fluorescent, Monodisperse Silica Spheres", Langmuir 1992, pp. 2921-2931.*
Kreuter, "Nanoparticles and Microparticles for Drug and Vaccine Delivery", J. Anat. vol. 189, 1996, pp. 503-505.*
Baker et al, Journal of Sol-Gel Science and Technology, 15, pp. 37-48, 1999.*
Rocha et al, Nanotechnology, 21, pp. 1-6, published Mar. 23, 2010.*
Tapec et al, Journal of Nanoscience and Nanotechnology, 2(3/4), pp. 405-409, 2002.*
Sokolov et al, Small 3(3), pp. 419-423, 2007.*
Yang et al., "Formation of Hollow Helicoids in Mosoporous Silica: Supramolecular Origami", Adv. Mater, 1999, 11, No. 17, pp. 1427-1431.
Sokolov and Kievsky, "3D Design of self-addembled nanoporous colloids", Studies in Surface and Catalysis, 156, 2005, pp. 433-442.
Sokolov et al., "Self-Assembly of Ultrabright Fluorescent Silica Particles", Small, 3, pp. 419-423, Jan. 24, 2007.
Anedda, A., Carbonaro, C. M., Clemente, E., Corpino, R., Grand!, S., Magistris, A. & Mustarelli, P. C. 2005. Rhodamine 6G-Si02 hybrids: A photoluminescence study. Journal of Non-Crystalline Solids, 351, 1850-1854.
Audebert, P., Bresson, E., Devillers, R. & Tribillon, G. 1996. Inclusion of fluorophores in hybrid sol-gel coatings; Application to in situ temperature measurements. Synthetic Metals, 81, 315-318.
Bagwe, R. P., Yang, C. Y., Hilliard, L. R. & Tan, W. H. 2004. Optimization of dye-doped silica nanoparticles prepared using a reverse microemulsion method. Langmuir, 20, 8336-8342.
Baker, G. A., Pandey, S., Maziarz, E. P. & Bright, E. V. 1999. Toward tailored xerogel composites: Local dipolarity and nanosecond dynamics within binary composites derived from tetraethylorthosilane and ORMOSILs, oligomers or surfactants. Journal of Sol-Gel Science and Technology, 15, 37-48.
Barret, E. P., Joyner, L. S. & Halenda, P. P. 1951. J. Am. Chem. Soc, 73, 373-380.
Calzaeerri, G., Bruhwiler, D., Megelski, S., Peenniger, M., Pauchard, M., Hennessy, B., Maas, H., Devaux, A. & Graf, U. 2000. Playing with dye molecules at the inner and outer surface of zeolite L. Solid State Sciences, 2, 421-447.
Calzaeerri, G., Huber, S., Maas, H. & Minkowski, C. 2003. Host-Guest Antenna Materials. Angew. Chem. Int. Ed., 42, 3732-3758.
Chan, W. C. W., Maxwell, D. J., Gao, X. H., Bailey, R. E., Han, M. Y. & Nie, S. M. 2002. Luminescent quantum dots for multiplexed biological detection and imaging. Current Opinion in Biotechnology, 13, 40-46.

Chan, W. C. W. & Nie, S. M. 1998. Quantum dot bioconjugates for ultrasensitive nonisotopic detection. Science, 281, 2016-2018.
Chen, X., Estevez, M. C, Zhu, Z., Huang, Y. E., Chen, Y., Wang, L. & Tan, W. 2009. Using Aptamer-Conjugated Fluorescence Resonance Energy Transfer Nanoparticles for Multiplexed Cancer Cell Monitoring. Anal Chem.
Del Monte, F. & Levy, D. 1998. Formation of fluorescent rhodamine B J-dimers in sol-gel glasses induced by the adsorption geometry on the silica surface. Journal of Physical Chemistry B, 102, 8036-8041.
Deshpande, A. V. & Kumar, U. 2002. Effect of method of preparation on photophysical properties of Rh-B impregnated sol-gel hosts. Journal of Non-Crystalline Solids, 306, 149-159.
Doering, W. E. & Nie, S. M. 2003. Spectroscopic tags using dye-embedded nanoparticles and surface-enhanced Raman scattering. Analytical Chemistry, 75, 6171-6176.
Eastman, P. S., Ruan, W. M., Doctolero, M., Nuttall, R., De Eeo, G., Park, J. S., Chu, J. S. E., Cooke, P., Gray, J. W., Li, S. & Chen, E. Q. E. 2006. Qdot nanobarcodes for multiplexed gene expression analysis. Nano Letters, 6, 1059-1064.
Edler, K. J., Reynolds, P. A!, Whitea, J. W. & Cookson, D. 1997. Diffuse wall structure and narrow mesopores in highly crystalline MCM-41 materials studied by X-ray diffraction../. Chem. Soc., Faraday Transactons, 93, 199-202.
Edwards, B. S., Oprea, T., Prossnitz, E. R. & Sklar, L. A. 2004. Flow cytometry for high-throughput, high-content screening. Curr Op in Chem Biol, 8, 392-8.
Frantz, R., Carbonneau, C, Granier, M., Durand, J. O., Lanneau, G. F. & Corriu, R. J. P. 2002. Studies of organic-inorganic solids possessing sensitive oligoarylene-vinylene chromophore-terminated phosphonates. Tetrahedron Letters, 43, 6569-6572.
Fritzler, M. J. 2006. Advances and applications of multiplexed diagnostic technologies in autoimmune diseases. Lupus, 15, 422-7.
Gao, X. H., Yang, L. L., Petros, J. A., Marshal, F. F., Simons, J. W. & Nie, S. M. 2005. In vivo molecular and cellular imaging with quantum dots. Current Opinion in Biotechnology, 16, 63-72.
Gonzalez-Buitrago, J. M. & Gonzalez, C. 2006. Present and future of the autoimmunity laboratory. Clin Chim Acta, 365, 50-7.
Halas, N. J. 2009. The photonic nanomedicine revolution: let the human side of nanotechnology emerge. Nanomedicine (Lond), 4, 369-71.
Han M. Y., G. X. H., Su J. Z., Nie S. 2001. Nature Biotechnology, 19, 631-635.
Iyer, S., Woodworth, C. D., Gaikwad, R. M., Kievsky, Y. Y. & Sokolov, I. 2009. Towards nonspecific detection of malignant cervical cells with fluorescent silica beads. Small, 5, 2277-2284.
Jokerst, J. V., Raamanathan, A., Christodoulides, N., Floriano, P. N., Pollard, A. A., Simmons, G. W-Wong, J., Gage, C., Furmaga, W. B., Redding, S. W. & McDevitt, J. T. 2009. Nano-bio-chips for high performance multiplexed protein detection: determinations of cancer biomarkers in serum and saliva using quantum dot bioconjugate labels. Biosens Bioelectron, 24, 3622-9.
Kim, S., Pudavar, H. E. & Prasad, P. N. 2006. Dye-concentrated organically modified silica nanoparticles as a ratiometric fluorescent pH probe by one- and two-photon excitation. Chemical Communications, 2071-2073.
Klonkowski, A. M., Kledzik, K, Ostaszewski, R. & Widernik, T. 2002. Spectral properties of bis-9-anthryl derivatives immobilised in silica xerogel. Colloids and Surfaces a-Physicochemical and Engineering Aspects, 208, 115-120.
Lauer, S. A. & Nolan, J. P. 2002. Development and characterization of Ni-NTA-bearing microspheres. Cytometry, 48, 136-145.
Leventis, N., Elder, I. A., Rolison, D. R., Anderson, M. L. & Merzbacher, C. I. 1999. Durable modification of silica aerogel monoliths with fluorescent 2,7-diazapyrenium moieties. Sensing oxygen near the speed of open-air diffusion. Chemistry of Materials, 11, 2837-2845.
Liew, M., Groll, M. C., Thompson, J. E., Call, S. L., Moser, J. E., Hoopes, J. D., Voelkerding, K., Wittwer, C. & Spendlove, R. S. 2007. Validating a custom multiplex ELISA against individual commercial immunoassays using clinical samples. Biotechniques, 42, 327-8, 330-3.

(56) References Cited

OTHER PUBLICATIONS

Lin, Y. S., Tsai, C. P., Huang, H. Y., Kuo, C. T., Hung, Y., Huang, D. M., Chen, Y. C. & Mou, C. Y. 2005. Well-ordered mesoporous silica nanoparticles as cell markers. Chemistry of Materials, 17, 4570-4573.

Marlow, F., McGehee, M. D., Zhao, D., Chmelka, B. E. & Stucky, G. D. 1999. Doped Mesoporous Silica Fibers: A New Laser Material. Adanced Materials, 11, 632-636.

Mirasoli, M., Guardigli, M., Simoni, P., Venturoli, S., Ambretti, S., Musiani, M. & Roda, A. 2009. Multiplex chemiluminescence microscope imaging of P16(INK4A) and HPV DNA as biomarker of cervical neoplasia. Anal Bioanal Che in, 394, 981-7.

Ow, H., Larson, D. R., Srivastava, M., Baird, B. A., Webb, W. W. & Wiesner, U. 2005. Bright and stable core-shell fluorescent silica nanoparticles. Nano Letters, 5, 113-117.

Rao, A. P. & Rao, A. V. 2003. Studies on the effect of organic additives on the monolithicity and optical properties of the rhodamine 6G doped silica xerogels. Materials Letters, 57, 3741-3747.

Santra, S., Zhang, P., Wang, K., Tapec, R. & Tan, W. 2001. Anal Chem., 73, 4988.

Shibata, S., Taniguchi, T., Yano, T. & Yamane, M. 1997. Formation of water-soluble dye-doped silica particles. Journal of Sol-Gel Science and Technology, 10, 263-268.

Sokolov, I. & Naik, S. 2008. Novel fluorescent silica nanoparticles: towards ultrabright silica nanoparticles. Small, 4, 934-9.

Suratwala, T., Gardlund, Z., Davidson, K., Uhlmann, D. R., Watson, J. & Peyghambarian, N. 1998. Silylated coumarin dyes in sol-gel hosts. 1. Structure and environmental factors on fluorescent properties. Chemistry of Materials, 10, 190-198.

Tan, W Wang, K. He, X. Zhao, X. J., Drake, T., Wang, L. & Bagwe, R. P. 2004. Bionanotechnology based on silica nanoparticles. Med Res Rev, 24, 621-38.

Wang, L. & Tan, W. H. 2006. Multicolor FRET silica nanoparticles by single wavelength excitation. Nano Letters, 6, 84-88.

Wang, L., Yang, C. & Tan, W. 2005. Dual-luminophore-doped silica nanoparticles for multiplexed signaling. Nano Lett, 5, 37-43.

Wang, L., Zhao,V., O'Donoghue, M. B. & Tan, W. 2007. Fluorescent nanoparticles for multiplexed bacteria monitoring. Bioconjug Che in, 18, 297-301.

Yang, P., Wirnsberger, G., Huang, H. C., Cordero, S. R., McGehee, M. D., Scott, B., Deng, T., Whitesides, G. M., Chmelka, B. F., Buratto, S. K. & Stucky, G. D. 2000. Mirrorless lasing from mesostmctured waveguides patterned by soft lithography. Science, 287, 465-8.

Zhao, X. J., Bagwe, R. P. & Tan, W. H. 2004. Development of organic-dye-doped silica nanoparticles in a reverse microemulsion. Advanced Materials, 16, 173-176.

\* cited by examiner

SYNTHESIS OF ULTRABRIGHT FLUORESCENT SILICA PARTICLES

CROSS REFERENCE

The present application claims priority to United States Provisional Patent Application 61/282,644 filed on Mar. 10, 2010 entitled "Syntheses of ultrabright fluorescent silica particles" and 61/457,086 filed on Dec. 22, 2010 entitled "Assembly of super-bright fluorescent silica particles using inorganic silica precursor" the content of which is relied upon and incorporated herein by reference in its entirety.

FIELD OF INVENTION

The field of the invention is fluorescent silica particles. In particular, the field of the invention includes the preparation of bright luminofores for tagging, tracing, labeling applications.

BACKGROUND

Fluorescence allows for the detection of very low amounts of fluorescent molecules due to a very high signal-to-noise ratio (the background is typically non-fluorescent). Fluorescent colloids—from nano to microns size particles are used in a broad range of applications involving tagging, tracing, labeling (Hasegawa et al., 2005, Edwards et al., 2004, Lizard et al., 2004, Meldal, 2002, Ohata et al., 2003, Iyer et al., 2009, Tan et al., 2004), and particularly in biological applications (Halas, 2009). Using various reactive moieties such as carboxylic acids, biotin, streptavidin, amine, thiol, maleimide, succinimide, etc., one can attach specific sensing molecules to a labeling colloid, such as antibodies, various proteins, peptides, nucleic acids, aptamers, small molecules, and even liposomes. The particles could be bioconjugated with multiple biomolecules for multimodal, multiplexed imaging of large molecules, cells, tissues, and animals (Chen et al., 2009, Doering and Nie, 2003, Dupuy et al., 2005, Eastman et al., 2006, Fritzler, 2006, Gao and Dave, 2007, Gao et al., 2005, Gonzalez-Buitrago and Gonzalez, 2006, Jokerst et al., 2009, Lauer and Nolan, 2002, Liew et al., 2007, Mirasoli et al., 2009, Wang and Tan, 2006a, Wang et al., 2005, Wang et al., 2007).

General Approach to Synthesize Fluorescent Colloidal Particles.

Fluorescence of colloidal particles is typically achieved through incorporating either inorganic or organic fluorescent dyes (or pigments, quantum dots) into the particle's material. While inorganic dyes are typically more stable, their limited variety, relatively low quantum yield, and compatibility are the issues restricting their broad application. Large varieties of organic dyes and their high quantum yield, make them attractive to be used in fluorescent particles. However, the problems of organic dyes are in their low photostability and frequent change of their fluorescence dependence on the chemistry of the environment. Incorporation of dyes into silica matrix seems to be one of most promising approaches because of the excellent sealing ability and wide compatibility of silica with other materials, including biocompatibility. Numerous attempts to embed organic dyes into silica xerogels and zeolites have reported (Rao and Rao, 2003, Klonkowski et al., 2002, Deshpande and Kumar, 2002, Leventis et al., 1999, del Monte and Levy, 1998, Suratwala et al., 1998, Calzaferri et al., 2003, Zhao et al., 2004, Santra et al., 2004). Silica has been material of choice due to its good biocompatibility, low toxicity, and ease of functionalization with sensing molecules.

To prevent leakage of the dyes out of the porous matrix of xerogels, dyes were typically covalently bound to the silica matrix (Audebert et al., 1996, Bagwe et al., 2004, Frantz et al., 2002, Leventis et al., 1999, Baker et al., 1999, Suratwala et al., 1998, Lin et al., 2005, Antonini et al., 2000). While the photostability of such materials is higher than the stability of pure dyes, it typically does not prevent bleaching substances (including oxygen), from penetration inside such a composite material. Moreover, in the case of xerogel, it is rather hard to make well defined particles out of xerogel, which prevents it from being used as labels. Fluorescent lasing dyes possess relatively high photostability and excellent quantum yield. Incorporation of such dyes into mesoporous patterned silica films (Yang et al., 2000) and silica rods (Marlow et al., 1999) to create a new laser material has been reported.

Fluorescent particles are widely manufactured, but the processes used for their production are often tightly held trade secrets. So far the brightest particles have been made of quantum dots incorporated into polymer matrix (See Han, et al. 2001). Incorporation of dyes and quantum dots into glass particles seems to be one of most promising because of excellent sealing ability of the glass and wide compatibility of glass with other materials.

High brightness of labeling silica particles is desirable to attain higher signal-to-noise ratio, and consequently, to increase the sensitivity and/or speed of detection. There have been many attempts to make fluorescent nanoparticles silica of high brightness (Shibata et al., 1997, Ow et al., 2005, Larson et al., 2003, Bagwe et al., 2004, Wang and Tan, 2006b, Zhao et al., 2004, Yang et al., 2003, Kim et al., 2006). Most of the approaches utilized the covalent coupling between fluorescent dye and silica. Recently, the use of tris(2,2A-bipyridyl)dichlororuthenium(II) hexahydrate (Rubpy) dye was reported to non-covalently dope silica nanoparticles (Santra et al., 2001). All of these particles showed brightness comparable with a single bright quantum dot at best.

Another approach, the synthesis of one-step self-assembly of nanoporous (sometimes called mesoporous) silica particles with physically encapsulated organic dyes was proposed (Naik and Sokolov, 2008, Sokolov et al., 2007) by the applicant. It is a templated sol-gel self-assembly of nanoporous particles with fluorescent dye added in a relatively large concentration (up to 0.01M) to the synthesizing bath. After completing the synthesis, the dye stays inside of self-sealed cylindrical nanochannels. The particles were up to two orders of magnitude brighter than polymeric particles of the same size assembled with quantum dots (ZnS-capped CdSe quantum dots) (Santra et al., 2001) (we called these particles "ultrabright" for the lack of a better term).

However, the particles synthesized in (Naik and Sokolov, 2008, Sokolov et al., 2007) were colloids of several microns in size, whereas most of bio-labeling application require nanosize particles. The efforts to scale the particles down to nanoscale were done in the by Sokolov and Naik (Sokolov and Naik, 2008). The reported brightness of ~30 nm silica mesoporous particles was so far only ~40% of the brightness of a capped water dispersible quantum dot (about the size of 5-60 nm (Biju et al., 2010) dependent on the fluorescent wavelength. In the same time, a simple geometrical extrapolation of the brightness attained in the micron size particles to the brightness of 30 nm silica particles gives us the value which is substantially higher than the brightness of a quantum dot. The culprit was presumably in the dye leaking out of the nanoparticles.

SUMMARY

The invention relates to a class of silica particles in which luminofore molecules are introduced into nanoscale (also called mesoscale) pores of the matrix of the silica particles. The said luminofore molecules are introduced in the concentrations that are well above the limit of quenching the luminescence in free solution. The said luminofore molecules are physically encapsulated inside the said nanoscale pores. Said encapsulation does not result in quenching of luminescence of the encapsulated molecules in the said high concentrations. This encapsulation is accomplished by controlling the particle architecture on the nanometer size scale and results in significant brightness enhancement compared to free dye (called ultrabright particles here after). It is therefore a principal object and advantage of the embodiments of the present invention to provide a method for the synthesis of ultrabright luminescent particles.

The embodiments of the invention provide a method of making luminescent homogenous nanoporous silica particles by mixing luminescent dyes and silica precursors (both organic and inorganic) in the presence of a template (form by a copolymer such as a pluronic acid or a surfactant) to form homogenous luminescent nanoporous silica particles.

It is another object and advantage of the embodiments of the present invention to provide a method for the synthesis of ultrabright luminescent silica particles, in which the silica matrix of the particles is modified in the way to prevent the leakage of the encapsulated dye.

Other objects and advantages of the embodiments of present invention will in part be obvious, and in part appear hereinafter.

There is a need for the following embodiments of the invention. Of course, the invention is not limited to these embodiments.

In one embodiment of the invention, the silica matrix of the particles is modified with the help of silica co-precursors, which are chosen out of the family of organosilanes.

In another embodiment of the invention, the said organosilanes are added to the synthesizing bath in the beginning of the synthesis (co-condensation method).

In another embodiment of the invention, the organosilanes are added to the synthesizing bath after a predefined time since the beginning of the synthesis (sequential-grafting method).

In another embodiment of the invention, the ultrabright luminescent particles have a size below 1000 nm (will be called nanoparticles hereafter). In another embodiment of the invention, ultrabright luminescent particles have the size above 1000 nm (will be called microparticles hereafter).

These and other features of the embodiments of the invention are set forth in the description which follows.

BRIEF DESCRIPTION OF THE DRAWINGS

These and other features, aspect, and advantages of the present invention will become better understood with regard to the following description, appended claims, and accompanying drawings where:

DETAILED DESCRIPTION

Figure 1:
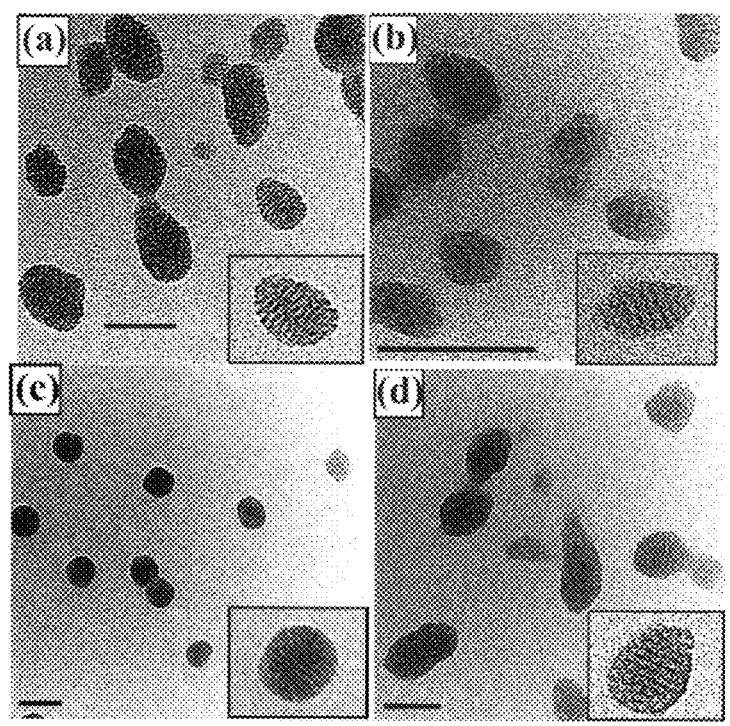
FIG. 1a-d show representative transmission electron microscopy (TEM) images for several fluorescent nanoporous silica nanoparticles. Respective images and the corresponding samples are listed in Table 1 as (a) TM91, (b) TM571, (c) TP91, and (d) TE91. The insets show enlarged particles. The scale bars are 50 nm.

The luminescent particles of the present invention include nanoporous (also called mesoporous) silica particles of the diameters ranging from tens of nanometers to tens of microns. The luminescence comes from luminescent dyes which are physically encapsulated inside nanopores of mesoporous silica matrix. Due to this specific nanoenvironment, the dye molecules do not quench its luminescence up to the concentrations which are substantially higher than the quenching concentration of free dye. Quantum yield of the dye remains sufficiently high to ensure ultrabrightness. The particle size (ranging from 10 nm to tens of microns) and the dye loading in the particles were controlled by the timing of the synthesis, the amount of the dye in the synthesizing bath, temperature, the amount of either alkaline or acidic catalyst, the synthesizing buffer, main silica precursor, and the amount of organosilanes added as co-precursor of silica. The use of organosilanes as co-precursor resulted in preventing the dye from leaking out of nanopores.

Particle Characterization

To demonstrate nanoscale porosity of the synthesized particles, transmission electron microscopy (TEM) imaging of the obtained particles was done.

The long-term stability of the particle's diameter and its colloidal suspension were measured by means of dynamic light scattering (DLS). Two kinds of particle diameters are studied: the most probable diameter (Dm) and the effective diameter (Deff). The most probable diameter represents the size of the most abundant particles in the suspension. The effective diameter defined by the diffusion coefficient was found from the analysis of self-c*orrelation function of intensities (number of photons) of the laser light scattered from the particles. The effective diameter can be considered an average one because the entire population of particles defines the scattered light. The difference between the most probable and effective diameters can be explained by multimodal size distributions of the particle sizes, which presumably occurs due to an agglomeration of smaller particles into larger aggregates. Even a small number of larger aggregates can substantially shift the average diameter towards larger values. Colloidal stability was monitored both visually and with the help of DSL. In the latter case, one can learn the stability of the suspension as well as the stability of the most probable diameter of the particles by monitoring the difference between the most probable and effective diameters.

An important property of the described ultrabrightness is the lack of quenching of fluorescence of the encapsulated dye inside the particles, which survives despite a relatively high concentration of the encapsulated dye. The absence of dimerization can be verified by recording the fluorescence spectra of the particles excited by different wavelengths.

Because fluorescent brightness is an important feature of the embodiments of the invention, it is worth describing the measurement protocol in more detail. A typical way to define the brightness of fluorescence is to use the molar absorptivity coefficient at the excitation wavelength (which in turn, relates to the absorbance cross-section) and the fluorescence quantum yield (Lakowicz, 2006). When dealing with particles, it is quite difficult to measure the actual absorbance of the dye inside the particles because of possible scattering of light by the particle's surface. When measuring the absorbance with UV-VIS spectroscopy, one indeed measures the extinction coefficient, which includes both absorbance and scattering. (As an example, one can see a strong extinction of ultraviolet light by silica nanoparticles (Sokolov and Naik, 2008) due to the Mia scattering, which could easily be confused with the absorbance). Furthermore, because the dye is an intrinsic part of the material at the nanoscale, the dye can change the scattering property of the surface. As a result, the standard approach of using optically "transparent medium" particles without a dye as a reference may not work correctly. Thus, it can be extremely tricky to separate the absorbance and scattering, and consequently to measure the true brightness using this approach. (Considering the particle's scattering as absorbance by mistake, one can get unrealistically high brightness.)

The most straightforward way, and physically unambiguous way to obtain the brightness of the synthesized particles is to measure the fluorescent brightness of the particles directly, by using a fluorescent spectrometer. To make these measurements independent of a particular spectrometer, the fluorescent brightness should be related to the brightness of a reference dye (the dye fluorescent of which is well known). The fluorescent brightness is the integral of the intensities of the fluorescent spectrum. Obviously, the fluorescence is collected from a known amount of the particles and fluorescent dye molecules. Hence, the brightness of each nanoparticle can be estimated by dividing the total brightness by the total amount of the particles (similar for the brightness of one reference dye molecule). This definition is free of any assumptions about the nanoparticles, amount of encapsulated dye molecules, light scattering, and quantum yield of the encapsulated dye. The only obvious restriction is to work in a low concentration of the particles and the reference dye, when the amount of fluorescence of the solution of the particles (the reference dye) is linearly proportional to the concentration of the particles (reference dye molecules). This is easy to check by sequential dilution of the particles (reference dye) solution, and measuring the corresponding decrease in fluorescence. The example below shows typical appropriate concentrations of the particles and the reference dye.

Using rhodamine 6G as the reference dye, and measuring fluorescence coming from the solution with known concentrations of particles and the reference dye, one can find the sought brightness of fluorescent silica nanoparticles (FSNP) relative to a single molecule of the reference dye as follows $$FSNP \text{ relative brightness} = (FL_{FSNP}/C_{FSNP})/(FL_{R6G}/C_{R6G}), \quad (1)$$

where $FL_{FSNP}$ ($FL_{R6G}$) is the (integral) amount of fluorescent light coming from a suspension of FSNP in water (or solution of reference R6G dye), $C_{FSNP}$ ($C_{R6G}$) is the density of FSNP (reference dye concentration) in the measured particle suspension (solution).

To be confident that the amount of measured fluorescence is directly proportional to the amount of the particles (particle's concentration), the measurements were done for a series of several concentrations.

The quantum yield (QY) of the dye encapsulated inside the particles can be found as follows $$QY = 95\% \frac{FL_{FSNP}}{A_{R6G \text{ of } FSNP}} \frac{A_{R6G}}{FL_{R6G}}, \quad (2)$$

where $A_{R6G \text{ of } FSNP}$ ($A_{R6G}$) is the absorbance of the R6G dye extracted from FSNP (R6G reference dye). 95% is the QY of R6G reference dye.

$A_{R6G \text{ of } FSNP}$ was found as follows. A small volume of FSNP colloidal suspension was dried and weighted as described above. Then, a small volume of the same FSNP suspension was dissolved using 1% hydrofluoric acid. $A_{R6G \text{ of } FSNP}$ was found by scaling up the concentration of R6G proportionally to the dissolution in the hydrofluoric acid solution.

The weight of the particles was found as follows. An aqueous suspension of particles in an aluminum foil cap was dried in a vacuum chamber for 24 h. As an example, weighing was carried out five times on a CAHN29 (CAHN Instruments Inc.) balance (sensitivity 0.1 µg).

Another weighing method can be done by means of quartz crystal microbalance. A predefined amount of water suspension of ultrabright particles is dried on the surface of a quartz crystal microbalance (as an example, QCM922, Princeton Applied Research, TN, USA). The mass of the particles is found from the change of resonance frequency of the QCM. The change of the weight, which is linearly proportional to the amount of dilution, indicates the proper work of the QCM method.

Characterizaton of micron size particles was done by electron microscopy (as an example, SEM: FEI Phenom). Using SEM-images we measure size of the particles. Prior to the measurements, the samples were coated with gold (as an example, for 1 minute in an Anatech hummer 6.2 sputtering system operating at 40 millitorr).

The measure of nanoporosity the particles, nitrogen adsorption/desorption isotherms of calcined nanoporous silica samples were measured (as an example, at 77 K on ASAP 2020 Porosimetry Analyzer (MicroMoretics)). In the example, the samples were degassed at 350° C. and 10 Pa for at least 12 h before the measurement.

The dye leakage tests were done using scanning laser confocal microscope (as an example, Nikon Eclipse C1). In this method, a gradient of concentration of glycerol water solution is created between two slides. It helps to "push" the dye molecules out of the channels, see references (Naik and Sokolov, 2008, Sokolov et al., 2007) for more detail.

Quantitative leakage of the dye can be verified by the comparing the maxima of luminescent intensities of the particles dispersed in aqueous medium. The encapsulated dye has the different wavelength of the luminescent maximum as compared to the dye in water. If the leakage happens, the maximum of the particles luminescence will shift towards the maximum of free dye as time goes.

EXAMPLES

Specific embodiments of the invention will now be further described by the following, nonlimiting examples which will serve to illustrate in some detail various features. The following examples are included to facilitate an understanding of ways in which an embodiment of the invention may be practiced. It should be appreciated that the examples which follow represent embodiments discovered to function well in the practice of the invention, and thus can be considered to constitute preferred mode(s) for the practice of the embodiments of the invention. However, it should be appreciated that many changes can be made in the exemplary embodiments which are disclosed while still obtaining like or similar result without departing from the spirit and scope of an embodiment of the invention. Accordingly, the examples should not be construed as limiting the scope of the invention.

Examples of Syntheses of Nanosized Particles.

Fluorescent nanoporous silica nanoparticles were prepared with a triethanolamine (TEA) additive as a catalyst, complexing agent, and pH stabilizer, Rhodamine 6G (R6G) as luminescent dye, tetraethyl orthosilicate (TEOS), and several organosilane co-precursor materials such as methyl trimethoxysilane (MTMS), ethyl triethoxysilane (ETES), and phenyl triethoxysilane (PTES). This experimental approach is mainly performed under the variation of parameters related to the timing of the synthesis, the amount of the dye in the synthesizing bath, temperature, the amount of either alkaline or acidic catalyst, the synthesizing buffer, main silica precursor, and the amount of organosilanes added as co-precursor of silica.

Tetraethyl orthosilicate (TEOS, Aldrich), methyltrimethoxysilane (MTMS, Aldrich), ethyl triethoxysilane (ETES, Aldrich), and phenyltriethoxysilane (PTES, Aldrich) were used as silica sources. Cetyltrimethylammonium chloride (CTAC, 25% aqueous solution, Aldrich) was used for as a structure-directing agent, and TEA (Aldrich) as an additive. Rhodamine 6G (R6G, Exciton Inc.) was used as a fluorescent dye. All the chemicals were used without further purification. Ultrapure de-ionized (DI) water from Mili-Q ultrapure system was used for all synthesis, dialysis, and storage steps.

Example A

Preparation of Fluorescent Mesoporous Nanoparticles Using Co-Condensation Method with a MTMS Organosilane Material The synthesis of the said fluorescent nanoporous nanoparticles was based on a relative molar composition of 1.0 total silanes: 0.2 CTAC: 0.02-0.04 R6G: 10.4 TEA: 141.6 $H_2O$ was used. In a typical synthesis of the nanoparticles TEOS, MTMS, and TEA were added and heated for 1 h at 90° C. without stirring. Another mixed water solution of R6G and CTAC, and was kept at 60° C. with stirring for 1 h. Two these kinds of solutions were mixed together and stirred for 5 h.

Example B

Preparation of Fluorescent Mesoporous Nanoparticles Using Sequential-Grafting Method with Organosilane Materials In a typical synthesis of ultrabright fluorescent silica nanoparticles TEOS and TEA were added and heated for 1 h at 90° C. without stirring. Another mixed water solution of R6G, CTAC, was kept at 60° C. with stirring. Two these kinds of solutions were mixed and stirred at room temperature. After stirring for 30 min, PTES co-precursor was added in the reacting mixture and followed by additional stirring for 4 h 30 min at room temperature.

The specification of chemical compounds used to synthesize the particles of examples A and B are listed in Table 1.

Example of General Cleaning Method of Fluorescent Mesoporous Nanoparticles.

CTAC surfactant, TEA, left-over silica precursors, and R6G dye in final UFSNP products were removed using a regular dialysis method. About 40 g of UFSNP solution product was dialyzed against deionized water using Spectra/Por® RC membrane, M.W. ~15,000 Da membrane until the supernatant water stopped showing any noticeable fluorescence.

To demonstrate mesoscale porosity of the synthesized nanoparticles, TEM imaging of the obtained particles was done. FIG. 1 presents the TEM images for several ultrabright silica nanoparticles prepared in this study; two large- and two small-size particles are shown. One can clearly see mesoporous structure of with slightly non-spherical particles. The particle specifications are listed in Table 1.

Characterization of the Exemplified Particles

Particle Sizes.

The long-term stability of the particle's diameter and its colloidal suspension were measured by means of dynamic light scattering (DLS). Table 2 shows the DLS results for the synthesized nanoparticles described in examples A and B and specified in Table 1. Two kinds of particle diameters are listed: the most probable diameter ($D_m$) and the effective diameter ($D_{eff}$) in Table 2 as defined above. Polydispersity shown in Table 2 is referred to the distribution of the most probable diameter. The difference between the most probable and effective diameters can be explained by multimodal size distributions of the particle sizes, which presumably occurs due to agglomeration of smaller particles into larger aggregates.

The stability depends on the particles concentration. The working concentrations were used as synthesized, which were relatively high (opaque solution). Visual monitoring of as prepared solution of the ultrabright nanoparticles showed formation of precipitants within one week (not shown). The supernatant colloidal suspension of the ultrabright nanoparticles was relatively stable for a much longer time (several weeks). However, the analysis of the zeta-potential (see later), indicates that the suspension cannot be stable for too long a time.

Figure 2:
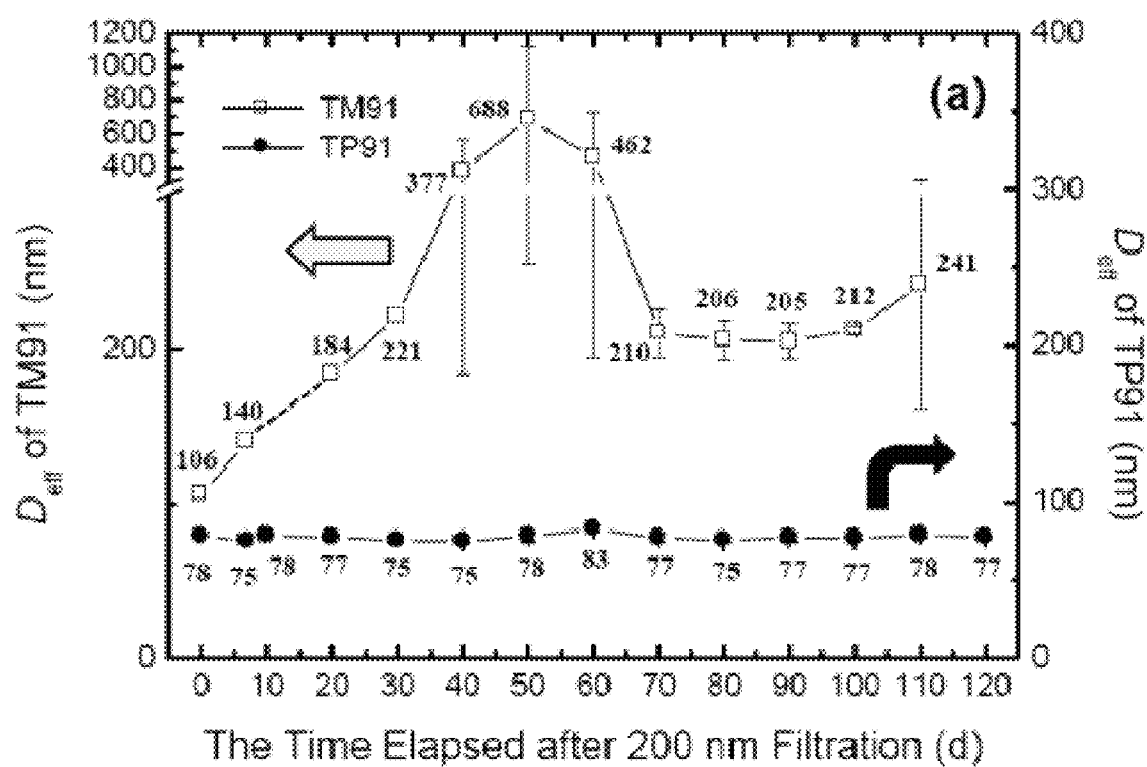
FIG. 2 demonstrates a representative example of dynamic light scattering (DLS) data for the effective diameter of the ultrabright particles according to the time elapsed after 200 nm filtration.

To do the DLS study, the ultrabright nanoparticles suspensions extracted by dialysis for 1 week were diluted with DI water by ten times and filtered using the 200 nm membrane filter to remove a small amount of probable agglomerates. The filtered UFSNP dispersions were kept in a quiescent condition while measuring DLS for 120 days. FIG. 2 illustrates two representative examples of the monitoring of the DLS-measured effective diameters. As an example, the corresponding concentrations of the synthesized particles were $1.14 \times 10^{-3}$ g/mL (TM91) and $2.81 \times 10^{-3}$ g/mL (TP91). One example demonstrates the most stable TP91 sample. The effective diameter remains constant for the entire duration of 120 days. Another example is a typical case of a less stable suspension of TM91 sample. One can see a gradual increase of the effective diameter to more than half of micron by 50 days. The observed decrease of the effective diameter after 50 days can be explained by precipitation of the formed agglomerates which were grown too large and could not be supported by the Brownian motion anymore (our measurements were done without re-suspending on the particle suspension, by sampling of the supernatant part of the suspension).

Fluorescent Properties of the Ultrabright Nanoparticles.

To find the brightness of the ultrabright particles, we typically measured the amount of fluorescence coming from 10 μL of the particle's stock suspension diluted in 3 mL of water. As an example for TM91 sample, this gave the integral fluorescence of $FL_{UFSNP}$ 8610 au (the error of fluorescence measurement was negligible). To find $C_{UFSNP}$, we weighted the stock suspension with the help of QCM. In our example of TM91, the found average was (1.14±0.15) mg of particles per 1 mL of water. Taking the known density of the nanoporous silica material (1.6 g/cm3 (Edler et al., 1997, Sokolov et al., 2007)), and the most abundant diameter of TM91 ultrabright particles (40 nm), we found that the density of nanoparticles in the measured suspension was $C_{FMSNP}$=(7.1±0.9)×1010 particles per 1 mL of water. Similarly, we found the brightness of single molecule of R6G dye. $FL_{R6G}$=7635 arbitral units (au) was coming from the dye concentration of (7.0±0.5)*10−8 M (found by using the Beer-Lambert law), or $C_{R6G}$=(4.2±0.3)×1013 dye molecules per 1 mL of water. Thus, formula (1) shows that the ultrabright particles fluorescent brightness of TM91 is equivalent to the brightness of approximately 670 molecules of free non-dimerized R6G dissolved in water. This can further be related to the brightness of, for example, a single ZnS-capped CdSe quantum dot (which is ~20 times brighter than a molecule of R6G (Chan et al., 2002, Chan and Nie, 1998)). This brings the brightness of TM91 ultrabright particles to 34× higher than a single quantum dot. Moreover, the ultrabright particles seem to be substantially brighter than other silica fluorescent nanoparticles reported in (Shibata et al., 1997, Ow et al., 2005, Larson et al., 2003, Bagwe et al., 2004, Wang and Tan, 2006b, Zhao et al., 2004, Yang et al., 2003, Kim et al., 2006), in which the brightness of the reported particles was similar to the fluorescence of one quantum dot.

Quantum yield of the dye encapsulated in the ultrabright nanoparticles was calculated using formula (2). A small volume of colloidal suspension of ultrabright particles was dried and weighted as described above. Then, a small volume of the same UFSNP suspension was dissolved using 1% hydrofluoric acid. It is useful to note that the extinction coefficient of R6G dye in water remains the same in the presence of 1% hydrofluoric acid (consequently one can use formula (2)). $A_{R6G \ of \ UFSNP}$ was found by scaling up the concentration proportionally to the dissolution in HF acid. As an example of TM91, we had $FL_{FMSNP}$=8610 au, $FL_{R6G}$=7635au, $A_{R6G \ of \ FMSNP}$=0.0074±0.0005, $A_{R6G}$ 0.0070±0.0005. This brings QY=1.0±0.1.

Estimation of the Amount of the Encapsulated Dye.

Using the method described in the previous paragraph, one can find the concentration of the dye encapsulated inside the particles. For example, with R6G dye it was found to be 9.3 mg/g (9.3 mg of dye per 1 g of particles) or 31 mM.

Table 3 shows the results of similar calculations made for the rest of our samples. One can see the concentration of R6G inside the particles ranging within 0.8-9.3 mg/g; the quantum yields of the encapsulated dye changes within 0.65-1.0. The particle's brightness varies from the 30 to 770× the brightness of individual free non-dimerized R6G dye molecules. This is also equivalent to the brightness of 1.5-39 CdSe/ZnS quantum dots.

Figure 3:
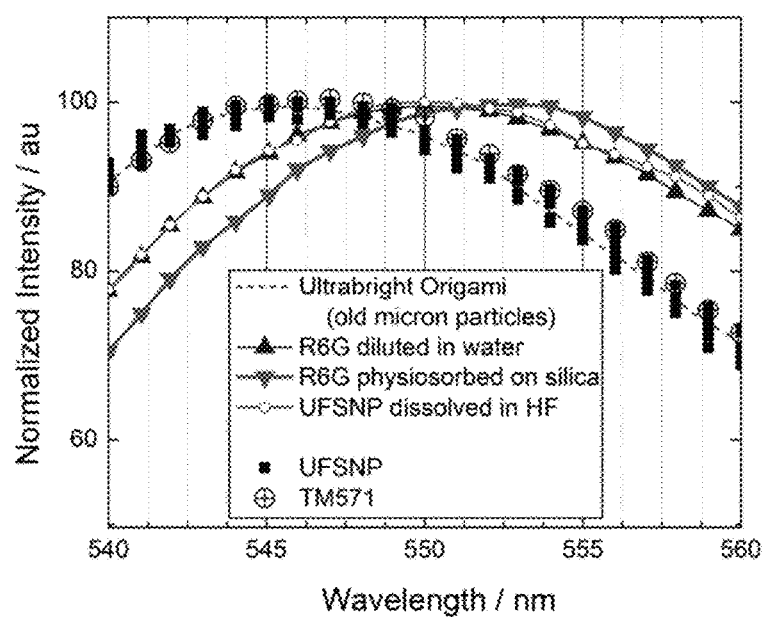
FIG. 3 illustrates high resolution fluorescent spectra of the ultrabright particles, ultrabright (origami) micron size particles, free rhodamine 6G (R6G) solution in water (1 µM), the ultrabright particles dissolved in 1% hydrofluoric acid HF solution, and R6G electrostatically physiosorbed on 60 nm solid silica particles. TM571 the ultrabright particles are shown separately as an example of the lowest quantum yield.

The above calculations were done based on the assumption of absence of free leaked dye in the solution used to measure the misunderstanding fluorescence. The results of both brightness and quantum yield would be biased if free dye were in the solution. Thus, it is important to check the absence of the leaked dye. This can easily be tested by looking at high-resolution fluorescence spectra near the maximum of fluorescence and monitoring the stability of the position of the spectral peaks in time. One can see that the aqueous solution of free dye shows the fluorescent maximum at 550 nm, as illustrated in FIG. 3 (solid curve). One can see that the fluorescence of the dye encapsulated inside of the particles has a characteristic blue shift of 5 nm. This can be explained by the presence of non-polar environment on the nanoporous channels (Cho et al., 2010, Sokolov and Naik, 2008) and caging effect (Anedda et al., 2005). This fact was used to distinguish between the dye encapsulated inside the particles and free dye.

]It should be noted that physical absorption of R6G dye on silica particles (Sokolov and Naik, 2008) leads to a quite visible red shift of the fluorescent maximum with respect to the free dye in water, which is illustrated in FIG. 3. It is interesting to note that TM571 sample, which has the lowest quantum yield, has also some visible red shift with respect to the other ultrabright nanoparticles. We believe that the decrease of quantum yield in this case is caused by the excessive physical interaction between R6G dye molecules and silica matrix of ultrabright nanoparticles (such a decrease is known in the case of interaction between fluorescent dyes and xerogel (Deshpande and Kumar, 2002, Suratwala et al., 1998)).

FIG. 3 illustrates another piece of useful information. One can see that after dissolution of the particles in HF, the resultant spectrum is virtually identical to the spectra of free dye. This fact justifies our use of the Beer-Lambert law to find the concentration of the dye inside of the particles after dissolving them in HF.

Figure 4:
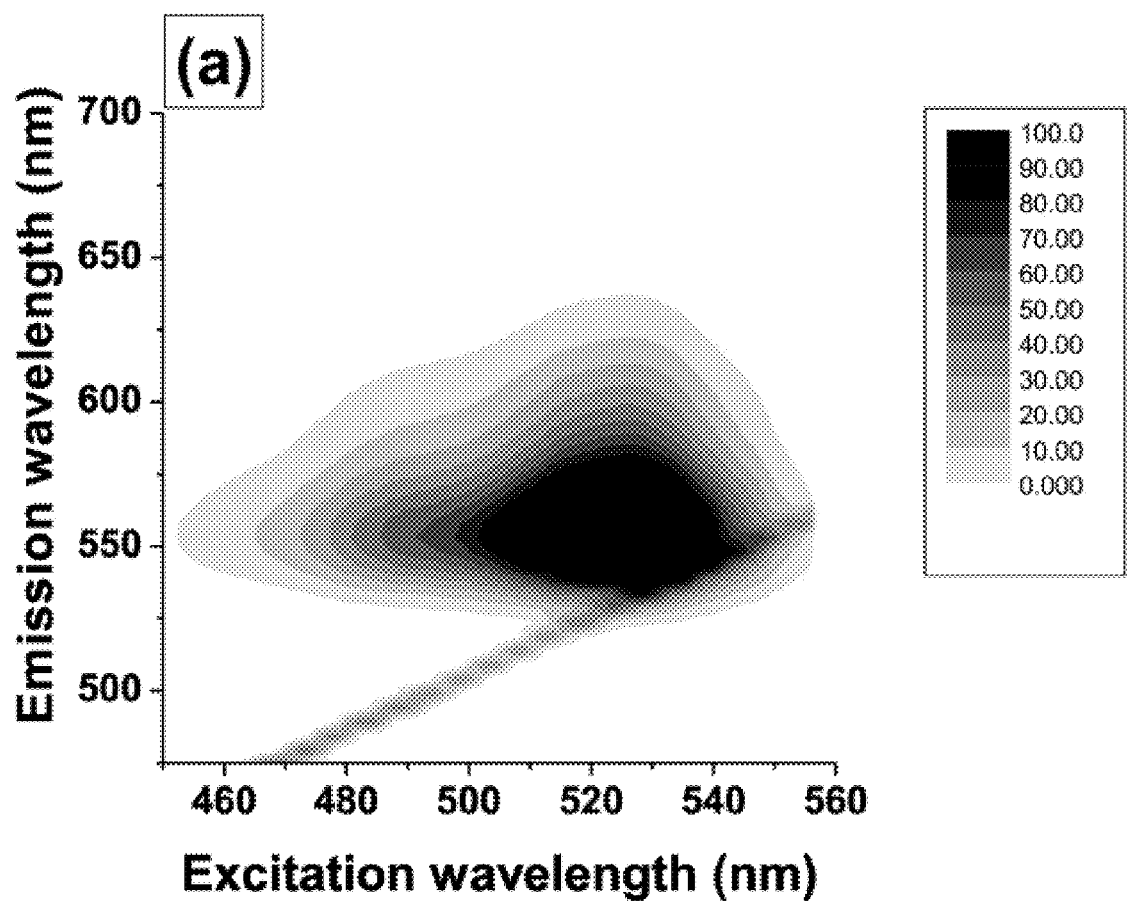
FIG. 4a-d exemplify the fluorescent spectra of ultrabright particles excited by different wavelengths. (a) free R6G dye in water demonstrating an example of dimerization (dye concentration is ~$1*10^{-5}$ M); (b) free R6G dye in water demonstrating an example of virtually no dimerization (dye concentration is (~$3*10^{-7}$ M); (c) The spectra corresponding to TM91/TE91/TP571 (the highest quantum yield). The spectra of these three samples are identical within the error of measurement; (d) TM571 (the lowest quantum yield).
Figure 4:
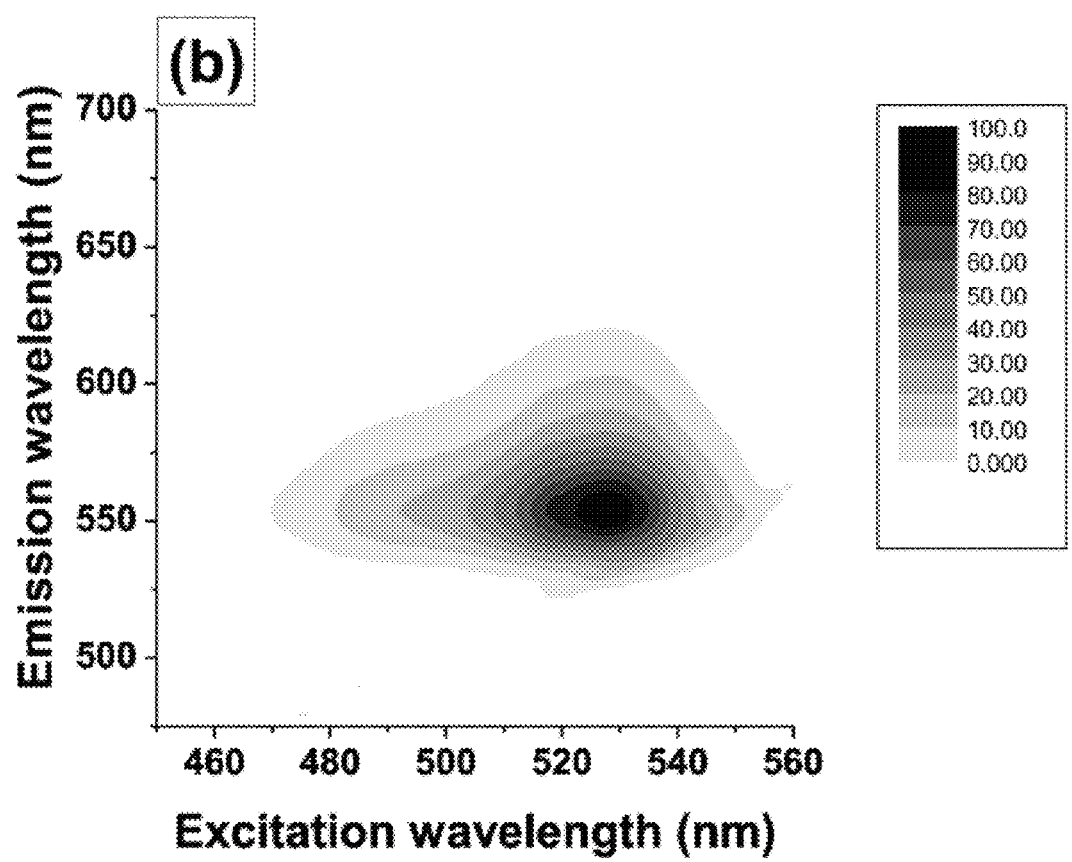
Figure 4:
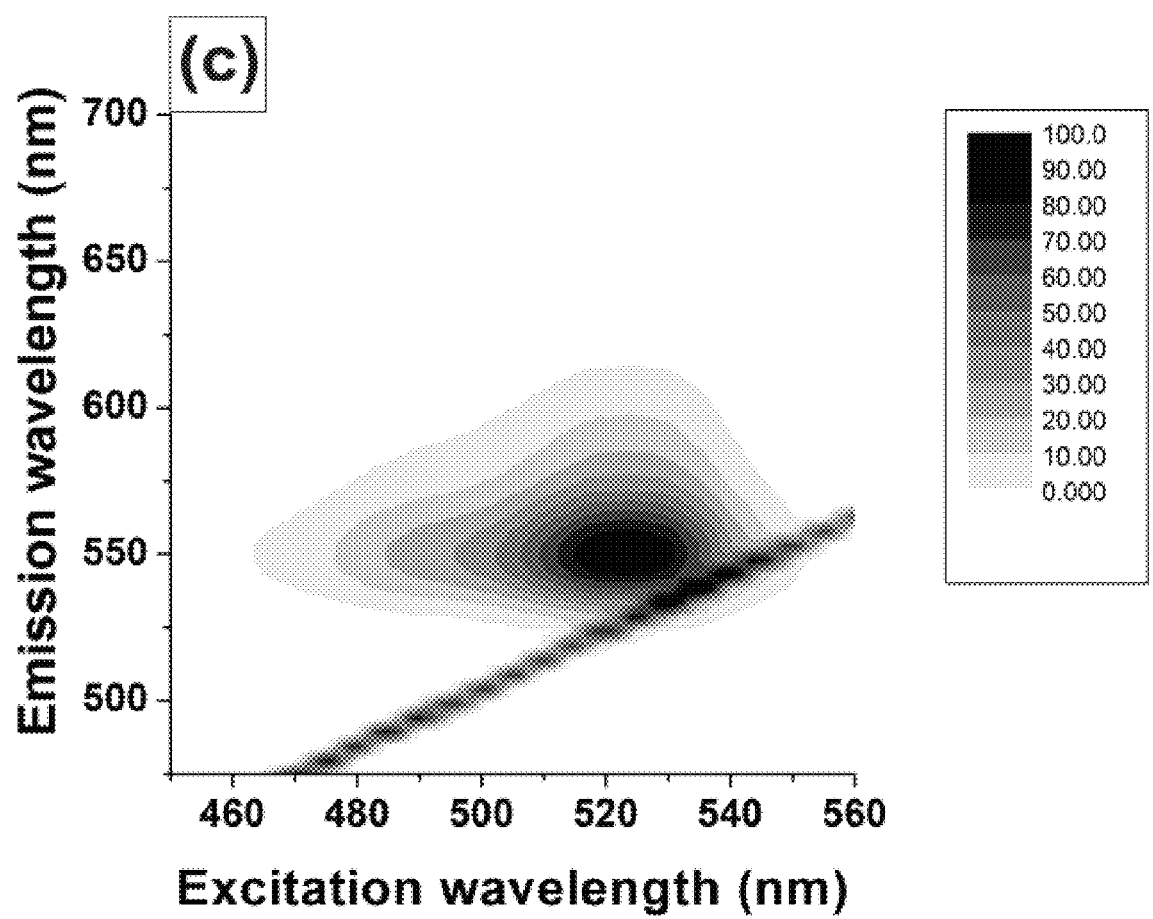
Figure 4:
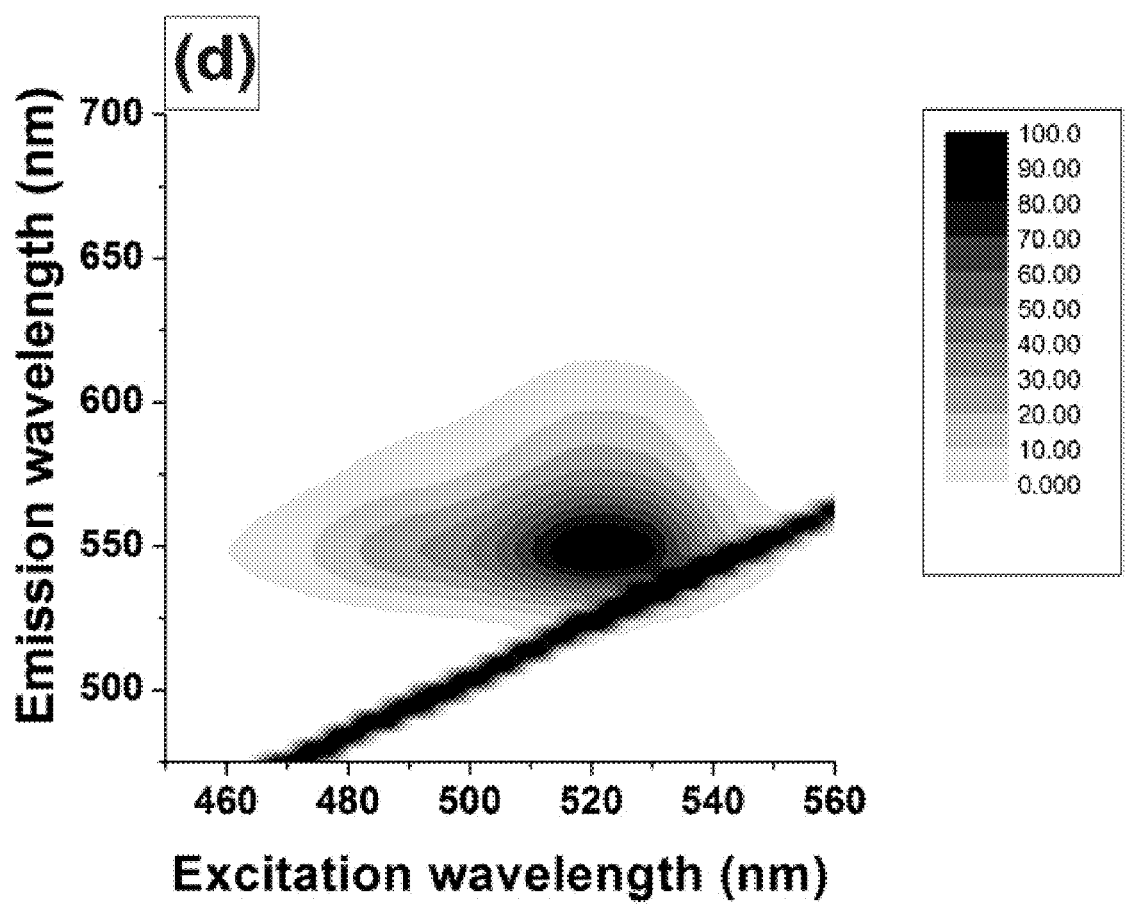

An important property of the described ultrabrightness is the lack of quenching of fluorescence of the encapsulated dye inside the particles, which survives despite a relatively high concentration of the encapsulated dye. The maximum concentration observed inside the reported particles is more than 5000 higher than the concentration of R6G dye in water which has no noticeable dimerization/self-quenching (dimerization happens before the fluorescent quench for the case of R6G dye). The absence of dimerization can be verified by recording the fluorescence spectra of the particles excited by different wavelengths. FIG. 4 illustrates several examples of such spectra corresponding to TM91/TE91/TP571 (identical spectra), TM571 (the lowest quantum yield), free R6G dye in water with and without dimerization/fluorescent quenching. One can see that the particles with high quantum yield do not show any visible traces of dimerization of dye molecules. Interestingly that there is virtually no noticeable dimerization/spectral broadening in the case of the low quantum yield of TM571. This implies that the decrease of the quantum yield for several ultrabright nanoparticles reported here comes mainly from the interaction between the dye molecules and silica matrix (as was shown above), rather than from the dye self-quenching of fluorescence.

Examples of Syntheses of Microsized Particles.

The particles were synthesized using disodium trioxosilicate ($Na_2SiO_3.9H_2O$, Fischer Scientific) as the silica source; cetyltrimethylammonium chloride (CTACl, 25% aqueous, Aldrich) as the structure directing agent (templating molecules) in the presence of hyrochloric acid (See J TBaker). Ethyltriethoxysilane (ETES) was used as a co-precursor of silica. In a typical synthesis, the molar ratio was as follows: 0.13 $Na_2SiO_3.9H_2O$: 100 $H_2O$: X R6G: 0.21 CTAC: 3.9 HCl: 0.0063 ETES, where X was in the range from $3 \cdot 10^{-3}$ to $9 \cdot 10^{-3}$. Disodium trioxosilicate, water, and dye were initially mixed and stirred for 15 min. CTAC (25% aqueous solution) and HCl (37%) were stirred separately for 2 min. Both solutions were then mixed and stirred for 5 min at room temperature. After keeping the mixture at 70° C. for 1 hour without stirring, ethyltriethoxysilane was added to the reacting mixture, additionally stirred at room temperature for a period of 30 minutes. The reactant solutions were kept at 70° C. for 3 hours under quiescent condition. The final product was collected by repeated centrifugation with the subsequent redispersion of the precipitate in a copious amount of distilled water.

Characterization of the Exemplified Particles

Figure 5:
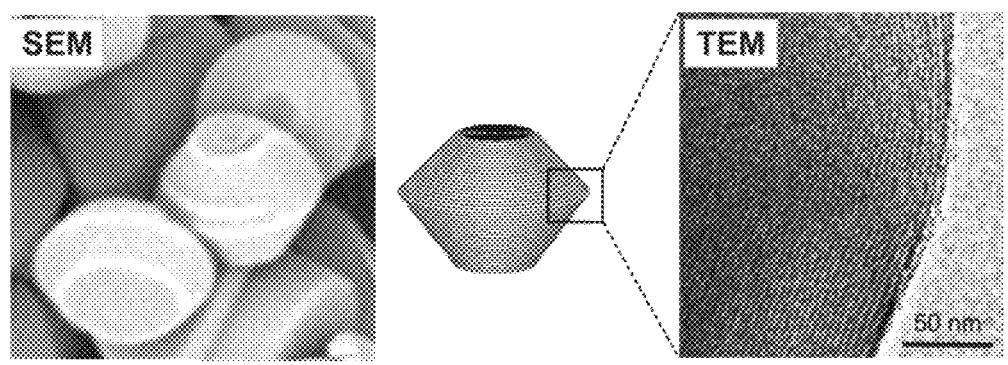
FIG. 5 illustrates scanning electron microscopy (SEM) image of a typical ultrabright fluorescent particles of micron size (left). A schematic of an ultrabright particle is shown in the middle. TEM image shows nanoporous structure of the particles (right).

FIG. 5 illustrates electron microscopy (SEM and TEM) images of the synthesized silica particles. The particles were 3.1±0.7 microns in size as estimated from the SEM images. The synthesized particles are complex nanostructured objects that can be described as tightly packed arrays/bundles of silica nanochannels/nanotubes. This is confirmed with the TEM in FIG. 2.

Figure 6:
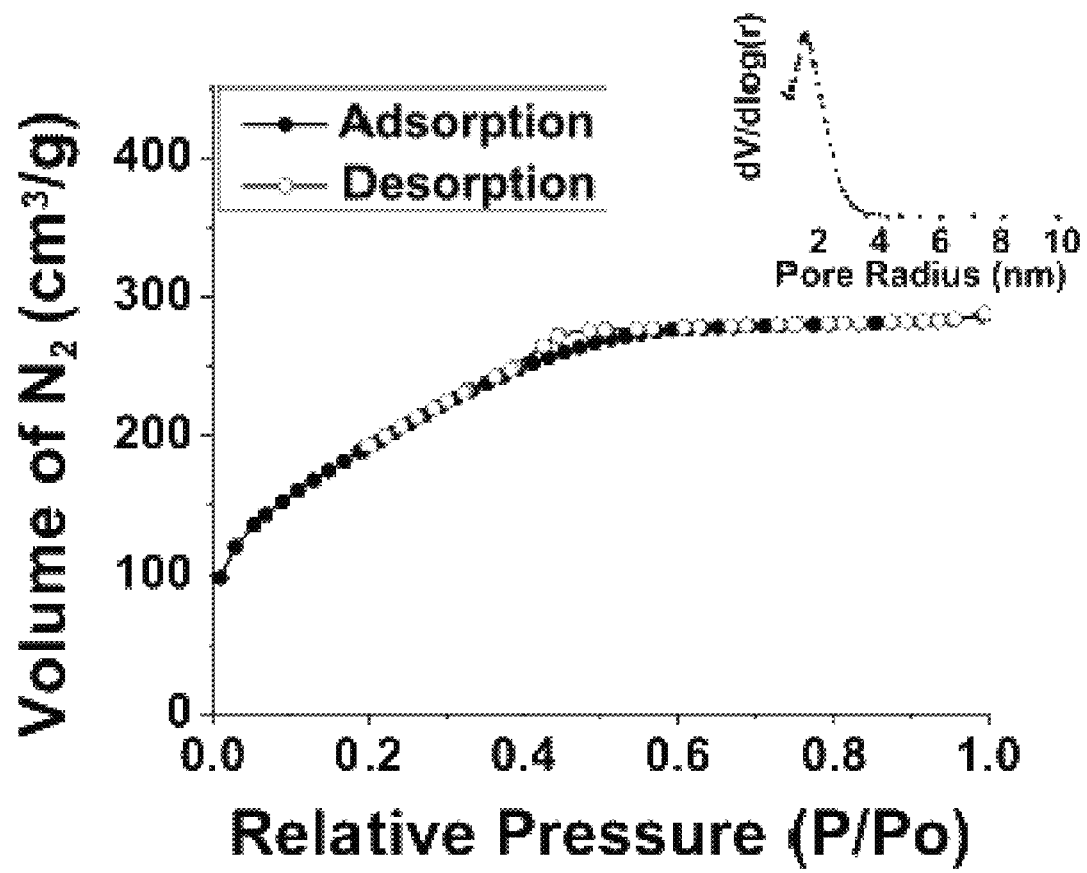
FIG. 6 illustrates the gas absorption analysis of the synthesized particles. Adsorption-desorption isotherms of silica ultrabright particles with different stirring time calcined at 450° C. Corresponding pore size distributions are shown as the inset.

Nanoporous structure of the synthesized particles was analyzed by the gas adsorption analysis. Nitrogen gas adsorption/desorption isotherms were measured for the calcined (at 450° C.) sample at 77° K. The results are shown in FIG. 6. This is a type IV isotherm is typical of high quality nanoporous materials. The diameter of pores was estimated from the adsorption branch of the isotherm according to the correlation obtained from BJH theory (Barret et al., 1951, Saito and Foley, 1991). It ranges in 3-4 nm. The the total pore volume 0.48 $cm^3/g$ and the BET surface area was 760 $m^2/g$.

Figure 7:
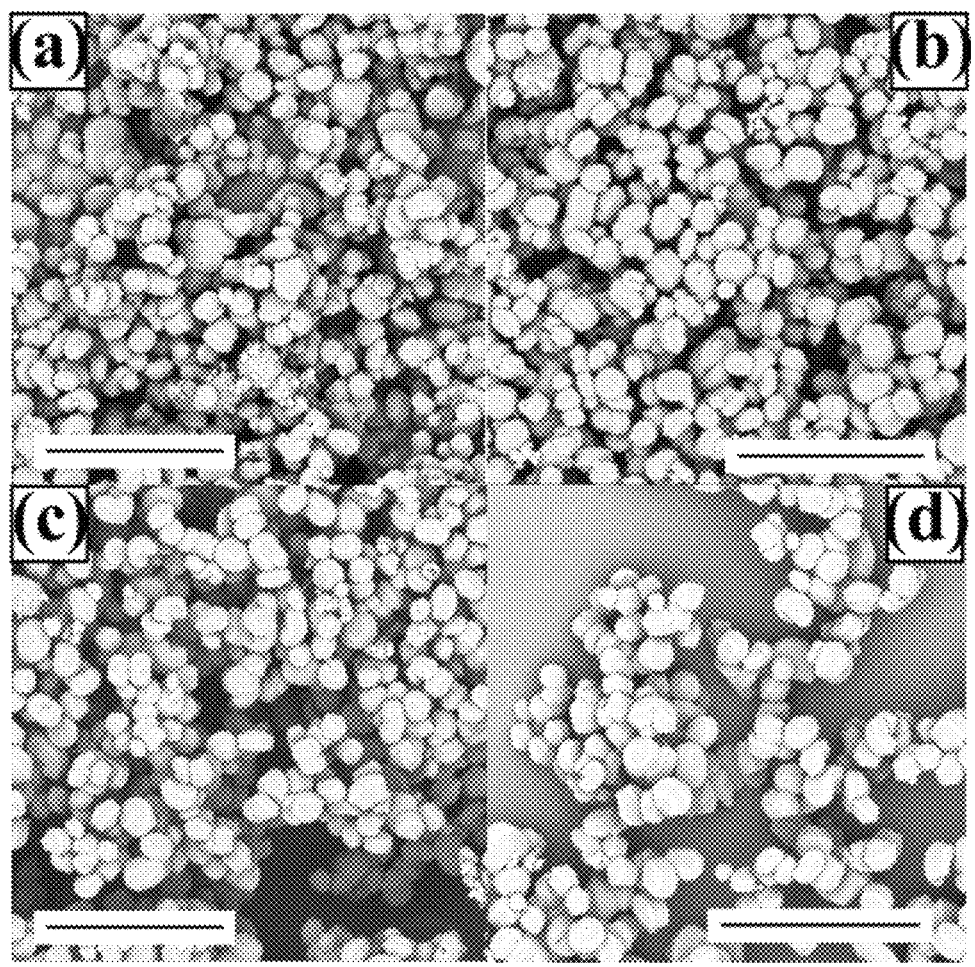
FIG. 7a-c illustrate SEM images of the synthesized ultrabright particles with different dye concentrations when (a) X=$3 \cdot 10^{-3}$, (b) X=$5 \cdot 10^{-3}$, (c) X=$7 \cdot 10^{-3}$, (d) X=$9 \cdot 10^{-3}$ of R6G. The scale-bar is 20 µm.

The amount of dye in the synthesizing bath was added in four different concentrations: $X=3 \cdot 10^{-3}$, $5 \cdot 10^{-3}$, $7 \cdot 10^{-3}$ and $9 \cdot 10^{-3}$ (X is defined in the used molar ratio 0.13 $Na_2SiO_3.9H_2O$:100 $H_2O$:X R6G: 0.21 CTAC:3.9 HCl: 0.0063 ETES). As one can see, the addition of dye results in the change in particle's shape rather than their size, see FIG. 7. There is a slight increase of the particle sizes for the highest concentration of R6G (FIG. 7 d). However, it is not far beyond one standard deviation of the size distribution.

Figure 8:
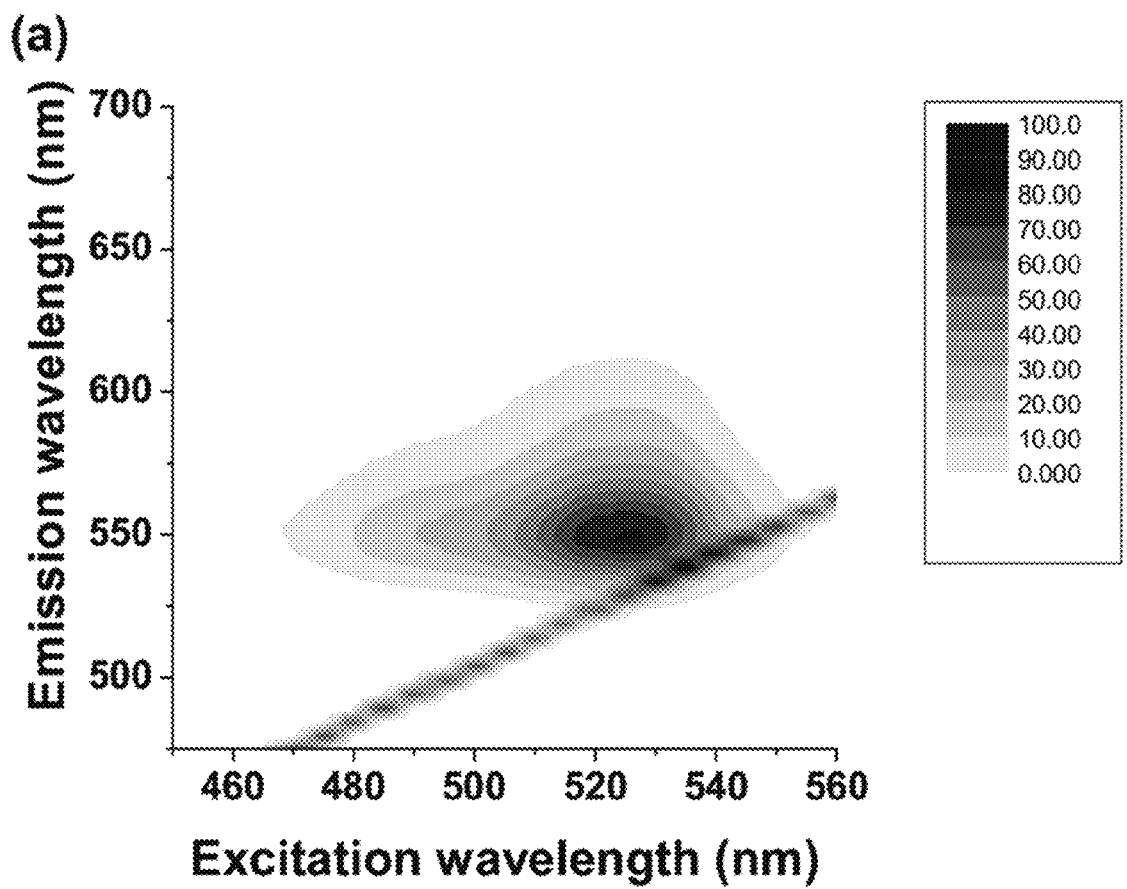
FIG. 8a-f illustrate the excitation-emission spectra of the synthesized discoids for different molar concentrations of the dye X=: (a) $3 \cdot 10^{-3}$, (b) $5 \cdot 10^{-3}$, (c) $7 \cdot 10^{-3}$, (d) $9 \cdot 10^{-3}$ of R6G. (e) shows an example of highly-diluted aqueous solution (~$3*10^{-7}$ M) of non-dimerized R6G dye. (f) An example of aqueous solution of partially dimerized R6G dye (~$1*10^{-5}$M concentration).
Figure 8:
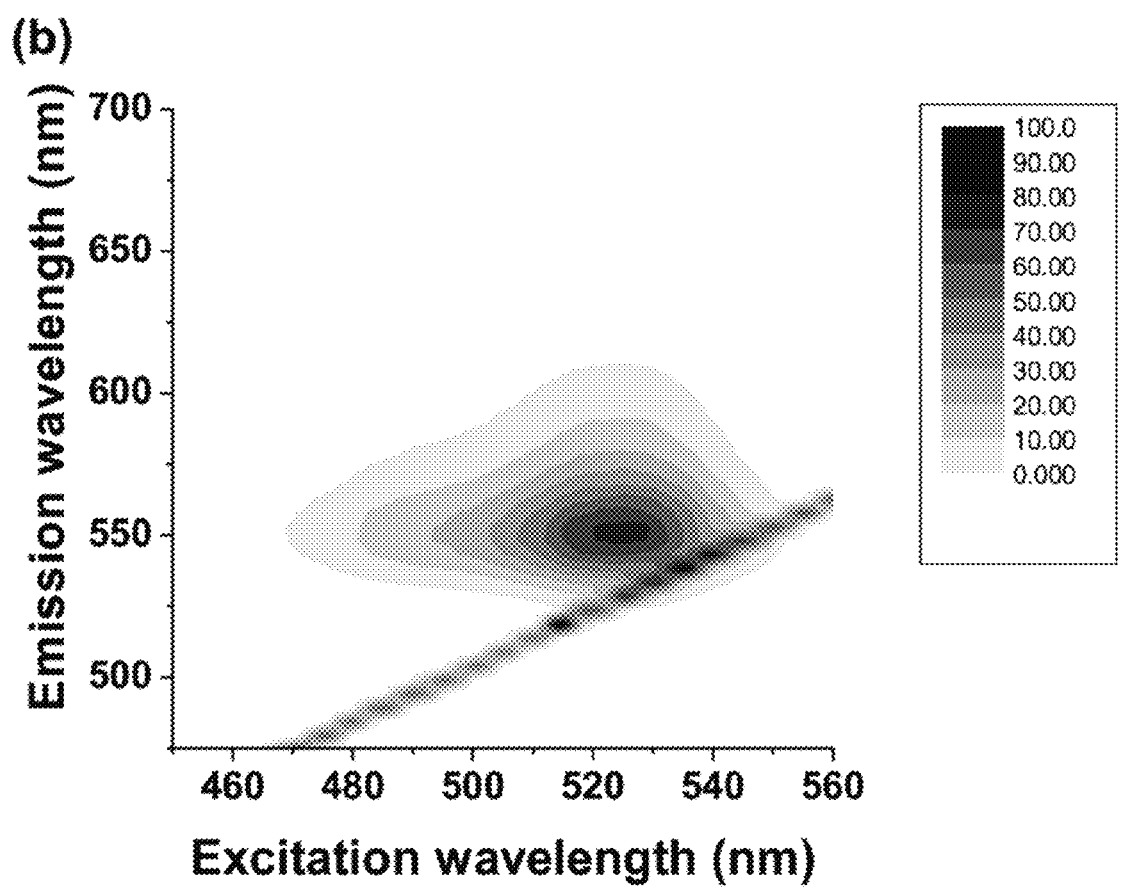
Figure 8:
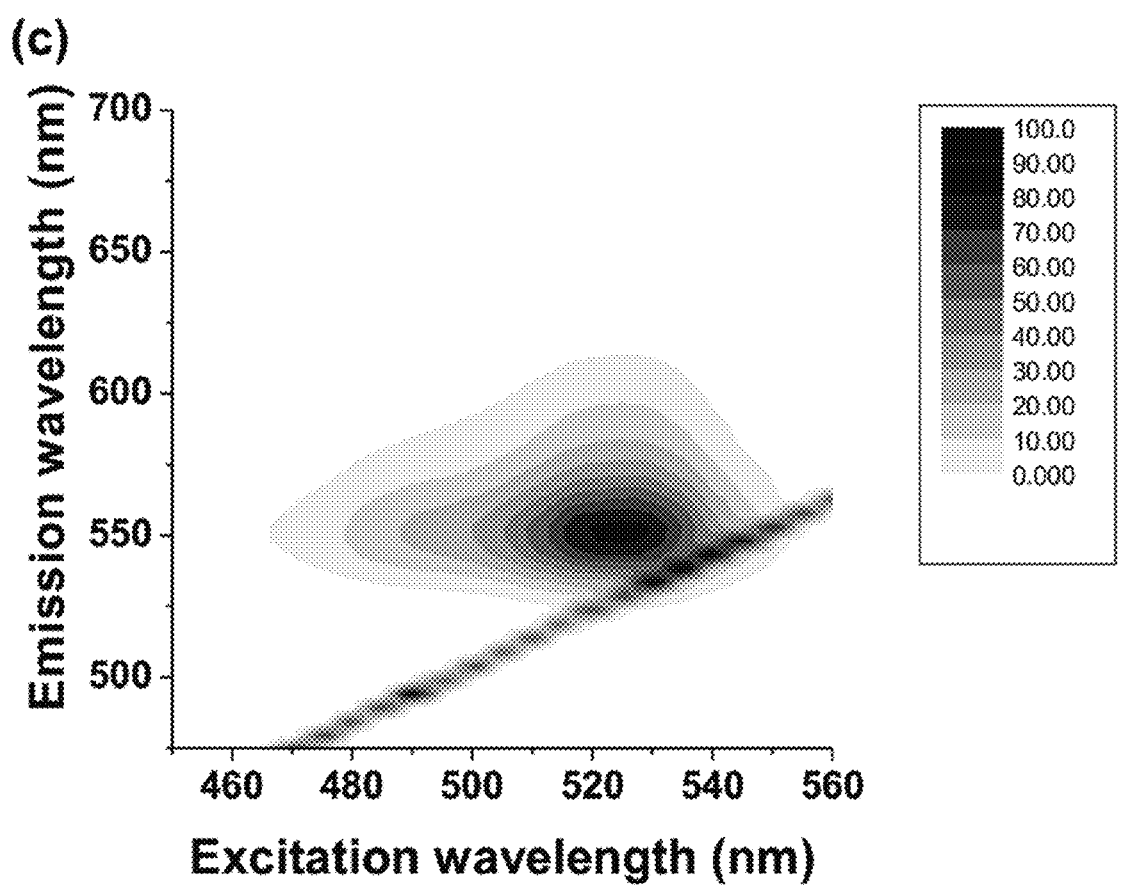
Figure 8:
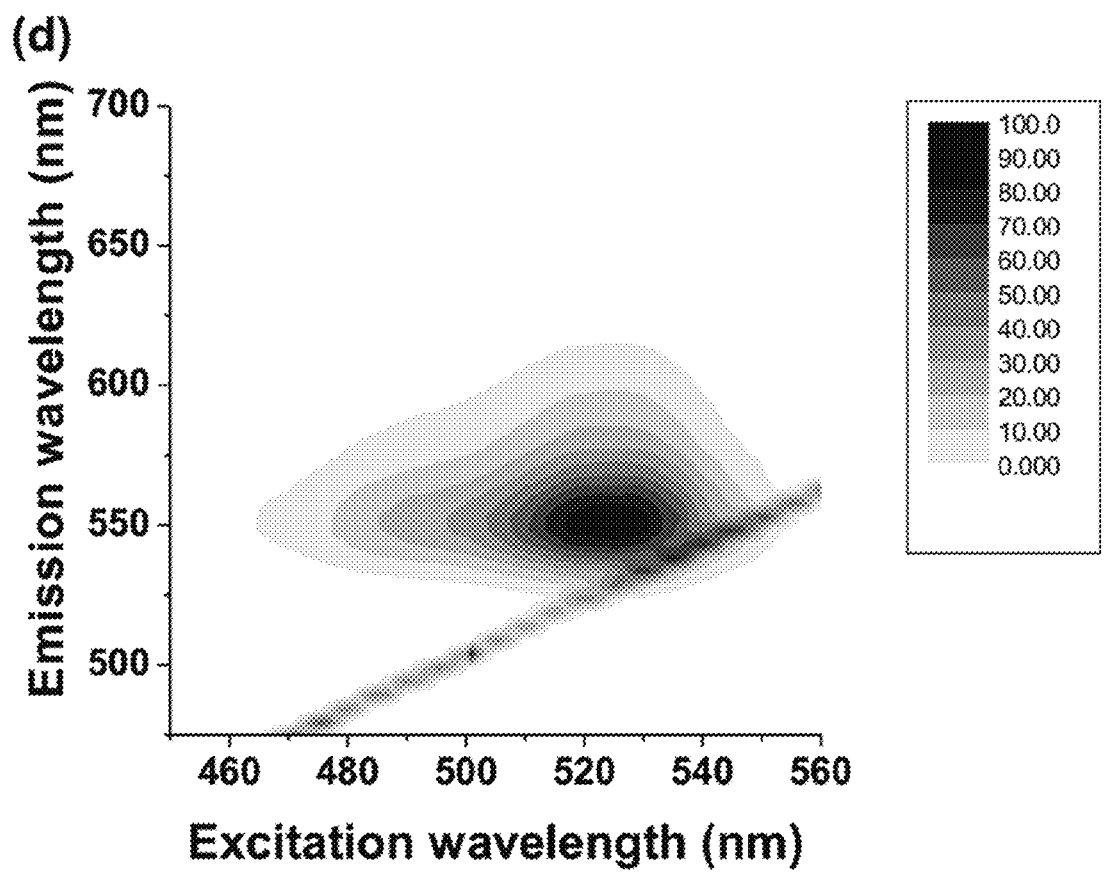
Figure 8:
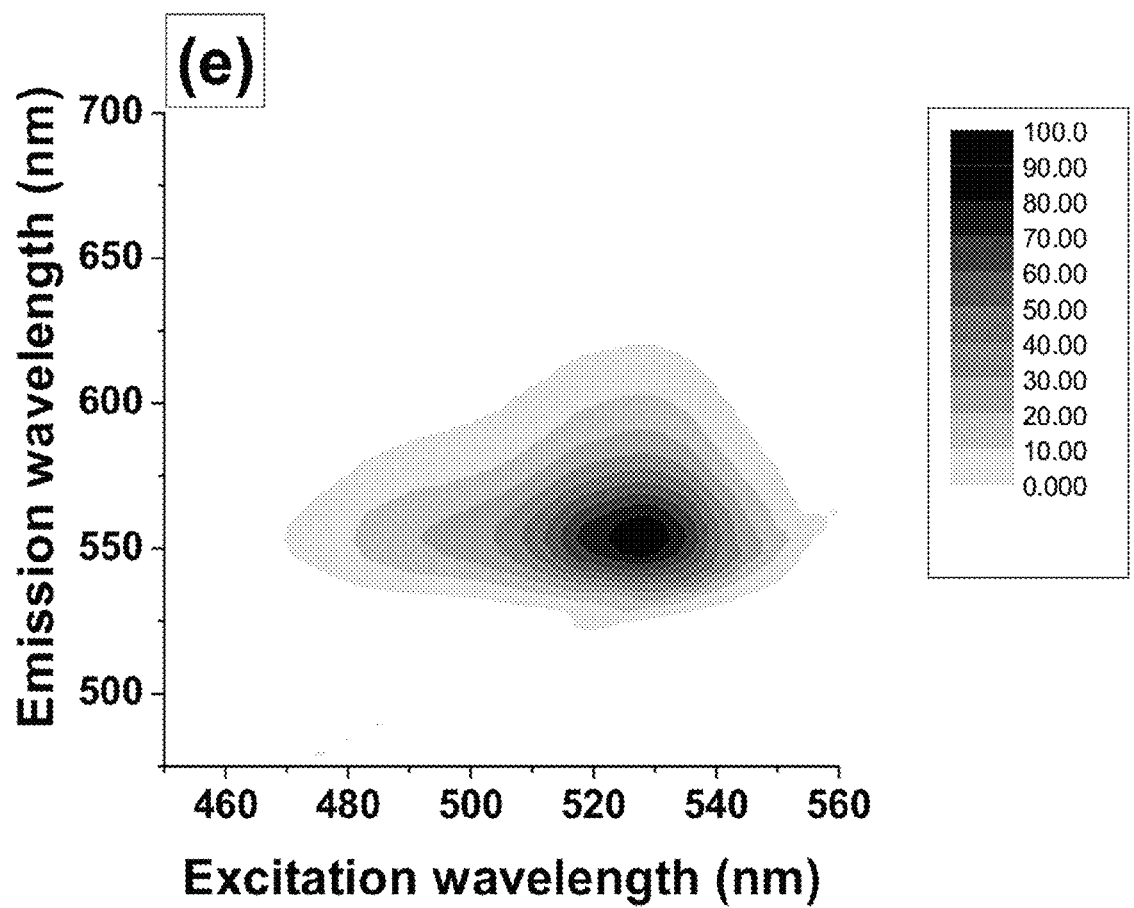
Figure 8:
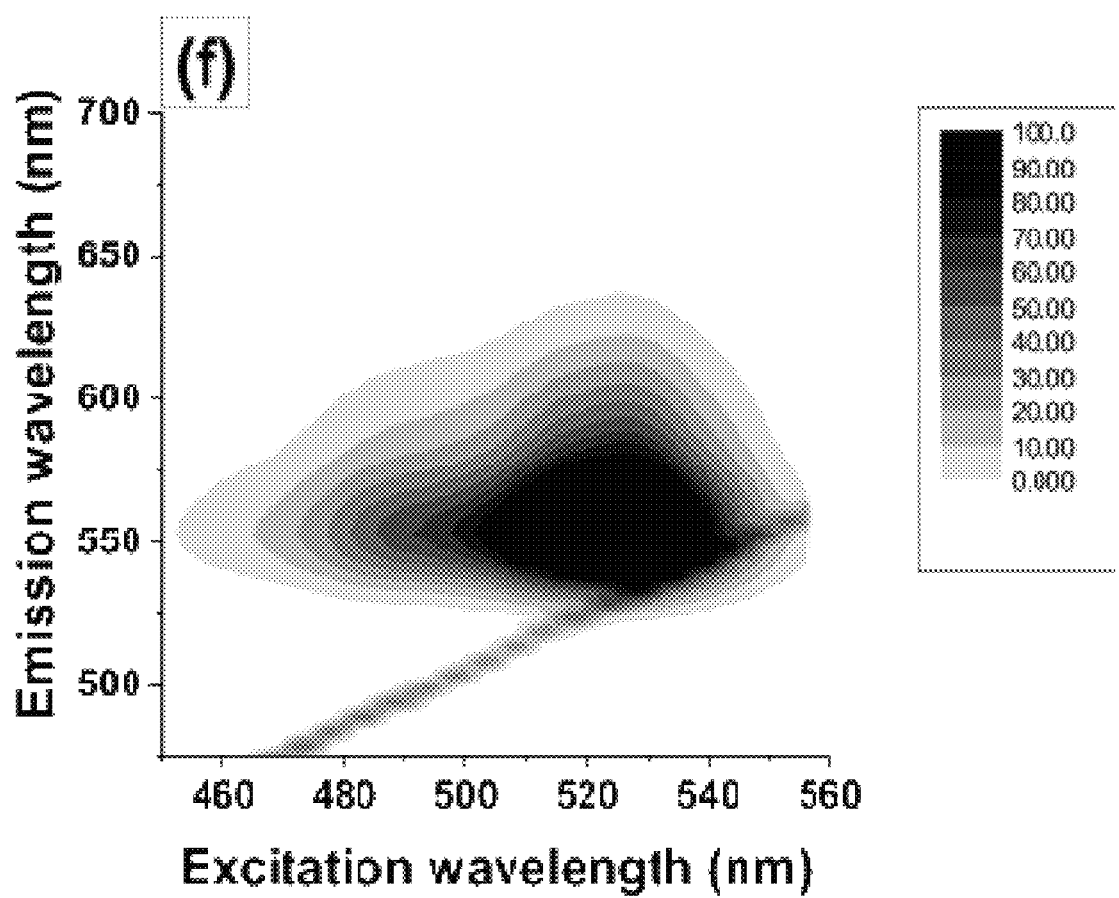

FIG. 8 illustrates the fluorescence spectra for the synthesized particles. Two samples with the lowest concentration, FIGS. 8 a and b illustrates the spectrum that is virtually indistinguishable from the spectrum of free non-dimerized R6G dye in water (FIG. 8e). For two other samples with the highest dye concentrations, the spectra are a little bit broadening with respect to the excitation. Such a behavior is typically related to either interaction of the dye with a substrate or partial dimerization of the dye (FIG. 8f) (Sokolov and Naik, 2008).

Figure 9:
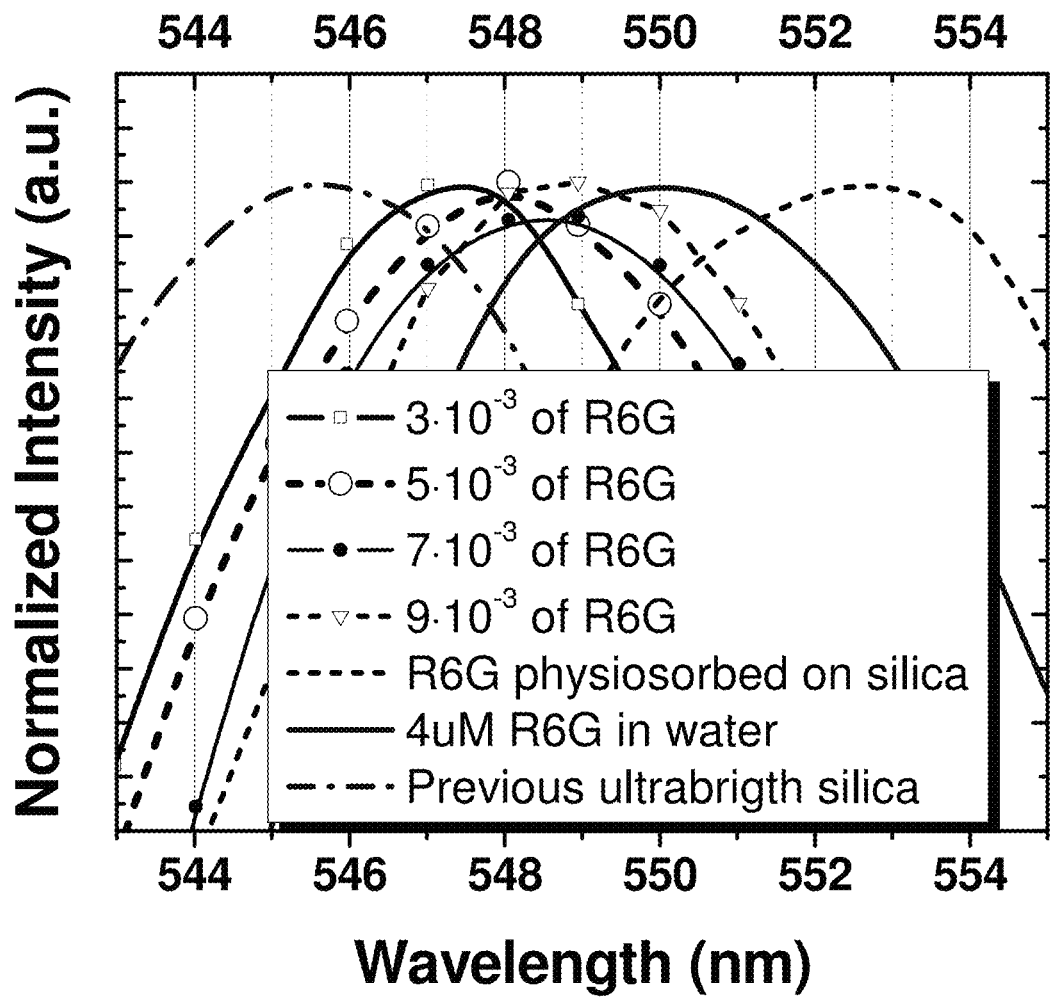
FIG. 9 illustrate the high-resolution fluorescent spectra of the synthesize particles near its maximum of fluorescence. One can see ~3 nm blue shift with respect to free R6G dye in aqueous environment, which indicates the presence of nonpolar environment surrounded the dye molecules.

The high-resolution fluorescent spectra of the synthesized particles near the maximum of fluorescence are illustrates in FIG. 9. Fluorescent peaks are also shown for free non-dimerized R6G dye, R6G dye physisorbed on 60 nm silica particles, and the ultrabright particles previously synthesized using organic precursors (Cho et al., 2010, Sokolov and Naik, 2008). A blue shift of 4.4 nm relative to free R6G dye in aqueous solution is expected for the ultrabright particles previously synthesized using organic precursors. This is mainly because the R6G molecules are captured inside of nonpolar environment of nanoporous channels, which is created by alkane chains of the templating surfactant molecules (Cho et al., 2010, Sokolov and Naik, 2008). Furthermore, as was previously shown, electrostatic absorbance of cationic R6G dye on silica surface results in approximately 3 nm red shift of fluorescent peak (Cho et al., 2010, Sokolov and Naik, 2008).

One can see that the fluorescence spectra recorded from the synthesized particles are blue-shifted with respect to the aqueous solution of free R6G dye to ca. 2.6, 2.0, 1.5, and 1.2 nm for the molar concentrations $X=3 \cdot 10^{-3}$, $5 \cdot 10^{-3}$, $7 \cdot 10^{-3}$, and $9 \cdot 10^{-3}$, respectively. (The position of the peaks was found by interpolation of the recorded data.) Thus, one can conclude that the R6G dye molecules encapsulated in pores are only partially staying within the nonpolar environment of nanoporous channels. A good portion of the molecules is interacting with the silica material of the particle's matrix as indicated by red-shift of the fluorescent maximum with respect to the previously reported ultrabright silica particles (Cho et al., 2010, Naik and Sokolov, 2008, Sokolov et al., 2007). The red shift, and consequently, the portion of strongly interacting molecules of R6G increases with the amount of the dye used in the synthesis (value X). It should be noted that the dye concentration is rather high inside the particles. Nevertheless, the amount of self-absorbance (Calzaferri et al., 2000) of the fluorescent light by R6G dye itself, which usually results in effective red shift of the spectral maximum, seems to be quite low. This can be seen, for example, from the comparison of the spectra coming from multi-micron (Sokolov et al., 2007) and nano (Cho et al., 2010)-size ultrabright particles, where the amount of self-absorbance should be quite different. This could presumably be explained by a) not-too-narrow Stock-shift of R6G dye, and b) still quite small distance of that light travel through the particles, even in the case of micron-sized particles.

To estimate the fluorescent brightness of the particles, we measured the fluorescence of a known amount of the particles. To evaluate the quantum yield of the encapsulated dye, we measured the brightness of the particles as well as the amount of the dye encapsulated in the particles. The measurements were done as described in the Experimental section by using equations (1) and (2). The total amount of dye trapped inside the nanoporous structures was found to be $0.3 \times 10^{-3}$ g/g (X=$3 \cdot 10^{-3}$ of R6G), $0.5 \times 10^{-3}$ g/g (X=$5 \cdot 10^{-3}$ of R6G), $0.6 \times 10^{-3}$ g/g (X=$7 \cdot 10^{-3}$ of R6G), and $0.8 \times 10^{-3}$ g/g (X=$9 \cdot 10^{-3}$ of R6G) of silica. The absorbance of the used concentrations of the dye needed for equations (1) and (2) is measured by UV-Vis spectroscopy using Beer-Lambert law. The data for four different samples are summarized in Table 4. *

To understand the brightness, it is informative to compare the brightness of the synthesize particles with the polymeric particles which contain a maximum possible amount of CdSe/ZnS (one of the brightest) quantum dots (Han M. Y., 2001). The brightness of those particles (Han M. Y., 2001) increased until the distance between quantum dots reached ~30 nm (the increase of the number of quantum dots would decrease fluorescence due to self-quenching). According to refs. (Chan and Nie, 1998, Chan et al., 2002), single ZnS-capped CdSe quantum dot is ~20× brighter than a free molecule of R6G. Keeping this maximum density of quantum dots, and scaling the particles to the diameter of 3.1 micron (to match the size of the particles synthesized here), one can find that our discoid particles are up to 6.7 times brighter than a similar size particle of assembled with the concentration of quantum dots giving the highest fluorescence. Therefore we can call them ultr$^a$bright (although it is still noticeably lower in brightness compared to what was reported in (Sokolov et al., 2007) for the particles synthesized using organic precursor). The brightness of the particles synthesized is up to 420 times higher than the fluorescence from the same volume of aqueous solution of free R6G dye (~10 µM).

Quantum yields of the synthesized particles with two lower dye concentrations are just a bit lower than that of free dye. The two high concentrations of dye led to a noticeable decrease of the quantum yield. Analysis of fluorescent spectra of the particles, as illustrated in FIG. 9, allowed us to conclude that the dye molecules interact with silica matrix of the synthesized discoids stronger compared to the case of ultrabright particles synthesized previously (Sokolov et al., 2007, Sokolov and Volkov, 2010) with organic silica precursor without ETES silica co-precursor. As a result, the quantum yield, and consequently the brightness of the encapsulated dye are expected to drop with the increase of dye concentration. Thus, the decrease of the quantum yield found for two high concentrations is in good agreement with the fluorescence spectra observation, which presumably comes from the stronger interaction of R6G dye molecules with the silica matrix. The other reason for the decrease of quantum yield could be in self-quenching of fluorescent dye molecules due to its close proximity. However, the excitation-emission spectra, as illustrated in FIG. 8, do not show any significant traces of dimerization of the dye. Such a dimerization should be seen for R6G dye before the fluorescence self-quenching. Therefore, we interpret that the observed decrease of quantum yield is caused by the excessive interaction of R6G dye molecules with the silica matrix.

Figure 10:
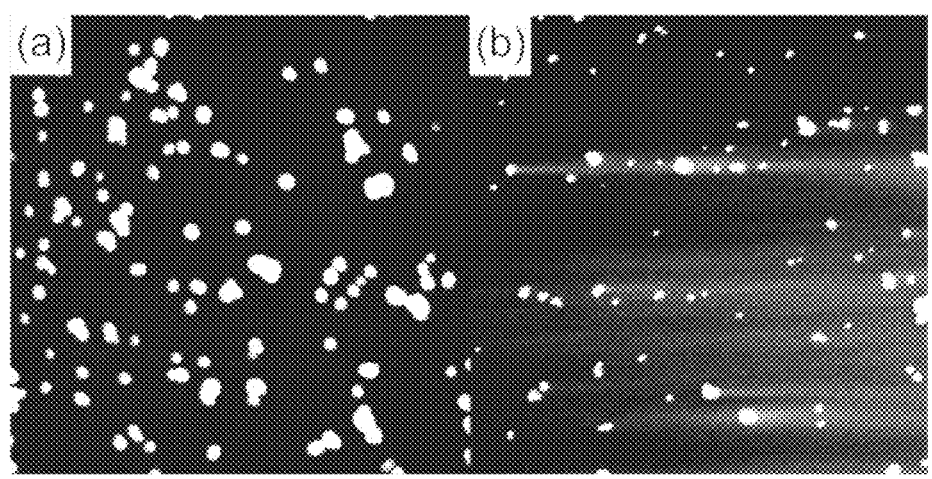
FIG. 10 exemplifies the leakage test for fluorescent discoids: (a) a representative confocal fluorescent image of the synthesized particles with ethyl triethoxysilane (ETES), (b) the same synthesis but no ETES silica co-precursor was added. The fluorescent tails of the dye leaked out of the particles are clearly seen in case (b).

To see the effect of addition of organic silica co-precursor, ETES on the dye leakage, we created a gradient of glycerol in water as described in (Naik and Sokolov, 2008, Sokolov et al., 2007) as illustrated in FIG. 10. The leakage of the dye out of the particles placed in the flow of gradient of water solution of glycerol concentration was imaged with the help of scanning laser confocal fluorescent microscopy. One can clearly see the tails of the leaked dye out of the particles without ETES co-precursor and no leakage when ETES was used.

The described embodiments and examples are illustrative only and not intended to be limiting. Although embodiments of the invention can be implemented separately, embodiments of the invention may be integrated into the system(s) with which they are associated. All the embodiments of the invention disclosed herein can be made and used without undue experimentation in light of the disclosure. The disclosed embodiments of the invention are not limited to those disclosed thereto. Embodiments of the invention are not limited by theoretical statements (if any) recited herein. The individual steps of embodiments of the invention need not be performed in the disclosed manner, or combined in the disclosed sequences, but may be performed in any and all manner and/or combined in any and all sequences. The individual components of embodiments of the invention need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials.

It can be appreciated by those of ordinary skill in the art to which embodiments of the invention pertain that various substitutions, modifications, additions and/or rearrangements of the features of embodiments of the invention may be made without deviating from the spirit and/or scope of the underlying inventive concept. All the disclosed elements and features of each disclosed embodiment can be combined with, or substituted for, the disclosed elements and features of every other disclosed embodiment except where such elements or features are mutually exclusive. The spirit and/or scope of the underlying inventive concept as defined by the appended claims and their equivalents cover all such substitutions, modifications, additions and/or rearrangements. Sub generic embodiments of the invention are delineated by the appended independent claims and their equivalents. Specific embodiments of the invention are differentiated by the appended dependent claims and their equivalents.

TABLE 1

Sample nomenclature and corresponding compositions of reagents used to synthesize fluorescent mesoporous silica nanoparticles by co-condensation and sequential-grafting methods.[a]

| sample | Additional organosilicas | 100 × [OS]/ [total silanes] (mol%) | $t_{ad}$ (min) | [R6G] (M) |
|---|---|---|---|---|
| TM10 | MTMS | 10 | 0 | $5 \times 10^{-3}$ |
| TM191 | MTMS | 5 | 30 | $5 \times 10^{-3}$ |
| TM91 | MTMS | 10 | 30 | $5 \times 10^{-3}$ |
| TM571 | MTMS | 15 | 30 | $5 \times 10^{-3}$ |
| TM91_60 | MTMS | 10 | 60 | $5 \times 10^{-3}$ |
| TE91 | ETES | 10 | 30 | $5 \times 10^{-3}$ |
| TP191 | PTES | 5 | 30 | $5 \times 10^{-3}$ |
| TP91 | PTES | 10 | 30 | $5 \times 10^{-3}$ |
| TP571 | PTES | 15 | 30 | $5 \times 10^{-3}$ |

[a]Notation: MTMS—methyl trimethoxysilane; ETES—ethyl triethoxysilane; PTES—phenyl triethoxysilane; OS—organosilane co-precursor materials;
$t_{ad}$ - the time lag for organosilane addition.

TABLE 2

Dynamic Light Scattering Results for UFSNP Using Co-Condensation and Sequential-Grafting Methods.[a]

| sample | $D_m$ (nm) | $D_{eff}$ (nm) | polydispersity |
|---|---|---|---|
| TM10 | 53 | 205 | 0.21 |
| TM191 | 36 | 150 | 0.20 |
| TM91 | 40 | 106 | 0.22 |
| TM571 | 23 | 140 | 0.20 |
| TM91_60 | 30 | 92 | 0.12 |
| TE91 | 52 | 88 | 0.19 |
| TP191 | 28 | 120 | 0.20 |
| TP91 | 45 | 78 | 0.15 |
| TP571 | 34 | 140 | 0.15 |

[a]$D_m$ - most probable diameter obtained from the multimodal size distribution results of dynamic light scattering device used in this study;
$D_{eff}$ - effective diameter.

TABLE 3

Properties for Fluorescent Mesoporous Silica Nanoparticles.[a]

| sample | $A_{UV(488\ nm),\ HF}$ | $F_{area,DI\ water}$ (AU) | $\Phi_{UFSNP}$ | $W_{dye/UFSNP}$ (mg/g) | Most probable diameter (nm) | Relative Brightness (# of R6G free molecules) |
|---|---|---|---|---|---|---|
| R6G $10^{-6}$ M | 0.007 | 7630 | 0.95 | n/a | n/a | 1 |
| TM10 | 0.013 | 10180 | 0.69 | 1.7 | 53 | 190 |
| TM191 | 0.008 | 7710 | 0.84 | 4.6 | 36 | 190 |
| TM91 | 0.0047 | 8610 | 1.01 | 9.3 | 40 | 670 |
| TM571 | 0.013 | 9640 | 0.65 | 7.0 | 23 | 58 |
| TM91_60 | 0.009 | 7660 | 0.78 | 5.7 | 30 | 130 |
| TE91 | 0.0067 | 7850 | 1.02 | 5.1 | 52 | 770 |
| TP191 | 0.005 | 4590 | 0.82 | 2.2 | 28 | 43 |
| TP91 | 0.0098 | 9980 | 0.89 | 2.5 | 45 | 211 |
| TP571 | 0.002 | 2145 | 0.98 | 0.8 | 34 | 32 |

[a]$A_{UV(488\ nm),\ HF}$ is the UV absorbance at a wavelength of 488 nm for UFSNP samples treated with HF 1 wt% solution.;
$C_{R6G\ in\ UFSNP}$ is the molar concentration for R6G dye inside UFSNPs, which were calculated with the UV absorbance based on the calibration curve (i.e. $C_{R6G\ in\ UFSNP}$ = ($A_{UV(488\ nm)}$ + 0.00215)/25890, r = 0.9995) of the UV spectrum of R6G according to concentration.;
$F_{area,\ DI\ water}$ is the integrated area of fluorescence emission spectra for UFSNP samples in aqueous solution.;
$\Phi_{UFSNP}$ is the quantum yields calculated using fluorescence emissions and UV absorbance based on the Rhodamine 6G $2.3 \times 10^{-7}$ M standard solution;
$W_{dye/UFSNP}$ is the mass of the R6G dye encapsulated inside 1 g of respective UFSNPs.

TABLE 4

Results for the synthesized ultrabright micron-size particles for the quantum yield, and brightness relative to free R6G molecules and the polymeric particles containing ZnS-capped CdSe quantum dot in the concentration giving the brightest fluorescence.

| R6G in synthesizing bath, (M) | R6G in particles mg per gram of silica | Quantum Yield | Brightness relative to free R6G molecules | Brightness relative to particle composed of QDs |
|---|---|---|---|---|
| $3 \cdot 10^{-3}$ | 1.5 ± 0.14 | 0.78 ± 0.12 | $3.4 \cdot 10^7$ | 3.3 ± 0.3 |
| $5 \cdot 10^{-3}$ | 1.7 ± 0.15 | 0.76 ± 0.12 | $4.0 \cdot 10^7$ | 3.8 ± 0.4 |
| $7 \cdot 10^{-3}$ | 3.6 ± 0.33 | 0.60 ± 0.11 | $6.2 \cdot 10^7$ | 6.0 ± 0.6 |
| $9 \cdot 10^{-3}$ | 3.7 ± 0.34 | 0.64 ± 0.11 | $7.0 \cdot 10^7$ | 6.7 ± 0.7 |

REFERENCES

ANEDDA, A., CARBONARO, C. M., CLEMENTE, F., CORPINO, R., GRANDI, S., MAGISTRIS, A. & MUSTARELLI, P. C. 2005. Rhodamine 6G-SiO2 hybrids: A photoluminescence study. *Journal of Non-Crystalline Solids*, 351, 1850-1854.

ANTONINI, J. M., HEMENWAY, D. R. & DAVIS, G. S. 2000. Quantitative image analysis of lung connective tissue in murine silicosis. *Experimental Lung Research*, 26, 71-88.

AUDEBERT, P., BRESSON, F., DEVILLERS, R. & TRIBILLON, G. 1996. Inclusion of fluorophores in hybrid sol-gel coatings; Application to in situ temperature measurements. *Synthetic Metals*, 81, 315-318.

BAGWE, R. P., YANG, C. Y., HILLIARD, L. R. & TAN, W. H. 2004. Optimization of dye-doped silica nanoparticles prepared using a reverse microemulsion method. *Langmuir*, 20, 8336-8342.

BAKER, G. A., PANDEY, S., MAZIARZ, E. P. & BRIGHT, F. V. 1999. Toward tailored xerogel composites: Local dipolarity and nanosecond dynamics within binary composites derived from tetraethylorthosilane and ORMOSILs, oligomers or surfactants. *Journal of Sol-Gel Science and Technology*, 15, 37-48.

BARRET, E. P., JOYNER, L. S. & HALENDA, P. P. 1951. *J. Am. Chem. Soc*, 73, 373-380.

BIJU, V., ITOH, T. & ISHIKAWA, M. 2010. Delivering quantum dots to cells: bioconjugated quantum dots for targeted and nonspecific extracellular and intracellular imaging. *Chem Soc Rev*, 39, 3031-56.

CALZAFERRI, G., BRUHWILER, D., MEGELSKI, S., PFENNIGER, M., PAUCHARD, M., HENNESSY, B., MAAS, H., DEVAUX, A. & GRAF, U. 2000. Playing with dye molecules at the inner and outer surface of zeolite L. *Solid State Sciences*, 2, 421-447.

CALZAFERRI, G., HUBER, S., MAAS, H. & MINKOWSKI, C. 2003. Host-Guest Antenna Materials. *Angew. Chem. Int. Ed.*, 42, 3732-3758.

CHAN, W. C. W., MAXWELL, D. J., GAO, X. H., BAILEY, R. E., HAN, M. Y. & NIE, S. M. 2002. Luminescent quantum dots for multiplexed biological detection and imaging. *Current Opinion in Biotechnology*, 13, 40-46.

CHAN, W. C. W. & NIE, S. M. 1998. Quantum dot bioconjugates for ultrasensitive nonisotopic detection. *Science*, 281, 2016-2018.

CHEN, X., ESTEVEZ, M. C., ZHU, Z., HUANG, Y. F., CHEN, Y., WANG, L. & TAN, W. 2009. Using Aptamer-Conjugated Fluorescence Resonance Energy Transfer Nanoparticles for Multiplexed Cancer Cell Monitoring. *Anal Chem*.

CHO, E. B., VOLKOV, D. O. & SOKOLOV, I. 2010. Ultrabright Fluorescent Mesoporous Silica Nanoparticles. *Small*, 6, 2314-2319.

DEL MONTE, F. & LEVY, D. 1998. Formation of fluorescent rhodamine B J-dimers in sol-gel glasses induced by the adsorption geometry on the silica surface. *Journal of Physical Chemistry B*, 102, 8036-8041.

DESHPANDE, A. V. & KUMAR, U. 2002. Effect of method of preparation on photophysical properties of Rh-B impregnated sol-gel hosts. *Journal of Non-Crystalline Solids*, 306, 149-159.

DOERING, W. E. & NIE, S. M. 2003. Spectroscopic tags using dye-embedded nanoparticles and surface-enhanced Raman scattering. *Analytical Chemistry*, 75, 6171-6176.

DUPUY, A. M., LEHMANN, S. & CRISTOL, J. P. 2005. Protein biochip systems for the clinical laboratory. *Clin Chem Lab Med*, 43, 1291-302.

EASTMAN, P. S., RUAN, W. M., DOCTOLERO, M., NUTTALL, R., DE FEO, G., PARK, J. S., CHU, J. S. F., COOKE, P., GRAY, J. W., LI, S. & CHEN, F. Q. F. 2006. Qdot nanobarcodes for multiplexed gene expression analysis. *Nano Letters*, 6, 1059-1064.

EDLER, K. J., REYNOLDS, P. A., WHITEA, J. W. & COOKSON, D. 1997. Diffuse wall structure and narrow mesopores in highly crystalline MCM-41 materials studied by X-ray diffraction. *J. Chem. Soc., Faraday Transactons*, 93, 199-202.

EDWARDS, B. S., OPREA, T., PROSSNITZ, E. R. & SKLAR, L. A. 2004. Flow cytometry for high-throughput, high-content screening. *Curr Opin Chem Biol*, 8, 392-8.

FRANTZ, R., CARBONNEAU, C., GRANIER, M., DURAND, J. O., LANNEAU, G. F. & CORRIU, R. J. P. 2002. Studies of organic-inorganic solids possessing sensitive oligoarylene-vinylene chromophore-terminated phosphonates. *Tetrahedron Letters*, 43, 6569-6572.

FRITZLER, M. J. 2006. Advances and applications of multiplexed diagnostic technologies in autoimmune diseases. *Lupus*, 15, 422-7.

GAO, X. H. & DAVE, S. R. 2007. Quantum dots for cancer molecular imaging. *Bio-Applications of Nanoparticles*, 620, 57-73.

GAO, X. H., YANG, L. L., PETROS, J. A., MARSHAL, F. F., SIMONS, J. W. & NIE, S. M. 2005. In vivo molecular and cellular imaging with quantum dots. *Current Opinion in Biotechnology*, 16, 63-72.

GONZALEZ-BUITRAGO, J. M. & GONZALEZ, C. 2006. Present and future of the autoimmunity laboratory. *Clin Chim Acta*, 365, 50-7.

HALAS, N. J. 2009. The photonic nanomedicine revolution: let the human side of nanotechnology emerge. *Nanomedicine (Lond)*, 4, 369-71.

HAN M. Y., G. X. H., SU J. Z., NIE S. 2001. *Nature Biotechnology*, 19, 631-635.

HASEGAWA, U., NOMURA, S. I., KAUL, S. C., HIRANO, T. & AKIYOSHI, K. 2005. Nanogel-quantum dot hybrid nanoparticles for live cell imaging. *Biochem Biophys Res Commun*, 331, 917-921.

IYER, S., WOODWORTH, C. D., GAIKWAD, R. M., KIEVSKY, Y. Y. & SOKOLOV, I. 2009. Towards nonspecific detection of malignant cervical cells with fluorescent silica beads. *Small*, 5, 2277-2284.

JOKERST, J. V., RAAMANATHAN, A., CHRISTODOULIDES, N., FLORIANO, P. N., POLLARD, A. A., SIMMONS, G. W., WONG, J., GAGE, C., FURMAGA, W. B., REDDING, S. W. & MCDEVITT, J. T. 2009. Nano-bio-chips for high performance multiplexed protein detection: determinations of cancer biomarkers in serum and saliva using quantum dot bioconjugate labels. *Biosens Bioelectron*, 24, 3622-9.

KIM, S., PUDAVAR, H. E. & PRASAD, P. N. 2006. Dye-concentrated organically modified silica nanoparticles as a ratiometric fluorescent pH probe by one- and two-photon excitation. *Chemical Communications*, 2071-2073.

KLONKOWSKI, A. M., KLEDZIK, K., OSTASZEWSKI, R. & WIDERNIK, T. 2002. Spectral properties of bis-9-anthryl derivatives immobilised in silica xerogel. *Colloids and Surfaces a-Physicochemical and Engineering Aspects*, 208, 115-120.

LAKOWICZ, J. R. 2006. *Principles of fluorescence spectroscopy*, New York, Springer.

LARSON, D. R., HEIKAL, A., OW, H., SRIVASTAVA, M., WIESNER, U., BAIRD, B. & WEBB, W. W. 2003. Development of fluorescent silica nanoparticles for biological imaging. *Biophysical Journal*, 84, 586a-586a.

LAUER, S. A. & NOLAN, J. P. 2002. Development and characterization of Ni-NTA-bearing microspheres. *Cytometry*, 48, 136-145.

LEVENTIS, N., ELDER, I. A., ROLISON, D. R., ANDERSON, M. L. & MERZBACHER, C. I. 1999. Durable modification of silica aerogel monoliths with fluorescent 2,7-diazapyrenium moieties. Sensing oxygen near the speed of open-air diffusion. *Chemistry of Materials*, 11, 2837-2845.

LIEW, M., GROLL, M. C., THOMPSON, J. E., CALL, S. L., MOSER, J. E., HOOPES, J. D., VOELKERDING, K., WITTWER, C. & SPENDLOVE, R. S. 2007. Validating a custom multiplex ELISA against individual commercial immunoassays using clinical samples. *Biotechniques*, 42, 327-8, 330-3.

LIN, Y. S., TSAI, C. P., HUANG, H. Y., KUO, C. T., HUNG, Y., HUANG, D. M., CHEN, Y. C. & MOU, C. Y. 2005. Well-ordered mesoporous silica nanoparticles as cell markers. *Chemistry of Materials*, 17, 4570-4573.

LIZARD, G., MONIER, S., PRUNET, C., DUVILLARD, L. & GAMBERT, P. 2004. [Microspheres, nanospheres and flow cytometry: from cellular to molecular analysis]. *Ann Biol Clin (Paris)*, 62, 47-52.

MARLOW, F., MCGEHEE, M. D., ZHAO, D., CHMELKA, B. F. & STUCKY, G. D. 1999. Doped Mesoporous Silica Fibers: A New Laser Material. *Advanced Materials*, 11, 632-636.

MELDAL, M. 2002. The one-bead two-compound assay for solid phase screening of combinatorial libraries. *Biopolymers*, 66, 93-100.

MIRASOLI, M., GUARDIGLI, M., SIMONI, P., VENTUROLI, S., AMBRETTI, S., MUSIANI, M. & RODA, A. 2009. Multiplex chemiluminescence microscope imaging of P16(INK4A) and HPV DNA as biomarker of cervical neoplasia. *Anal Bioanal Chem*, 394, 981-7.

NAIK, S. P. & SOKOLOV, I. 2008. Ultra-bright fluorescent silica particles: physical entrapment of fluorescent dye rhodamine 640 in nanochannels. In: NAGARAJAN, R. (ed.) *Nanoparticles: Synthesis, Stabilization, Passivation and Functionalization*. ACS.

OHATA, H., YAMADA, H., NIIOKA, T., YAMAMOTO, M. & MOMOSE, K. 2003. Optical bioimaging: from living tissue to a single molecule: calcium imaging in blood vessel in situ employing two-photon excitation fluorescence microscopy. *J Pharmacol Sci*, 93, 242-7.

OW, H., LARSON, D. R., SRIVASTAVA, M., BAIRD, B. A., WEBB, W. W. & WIESNER, U. 2005. Bright and stable core-shell fluorescent silica nanoparticles. *Nano Letters*, 5, 113-117.

RAO, A. P. & RAO, A. V. 2003. Studies on the effect of organic additives on the monolithicity and optical properties of the rhodamine 6G doped silica xerogels. *Materials Letters*, 57, 3741-3747.

SAITO, A. & FOLEY, H. C. 1991. *AIChE Journal*, 37, 429.

SANTRA, S., XU, J., WANG, K. & TAN, W. 2004. Luminescent nanoparticle probes for bioimaging. *J Nanosci Nanotechnol*, 4, 590-9.

SANTRA, S., ZHANG, P., WANG, K., TAPEC, R. & TAN, W. 2001. *Anal. Chem.*, 73, 4988.

SHIBATA, S., TANIGUCHI, T., YANO, T. & YAMANE, M. 1997. Formation of water-soluble dye-doped silica particles. *Journal of Sol-Gel Science and Technology*, 10, 263-268.

SOKOLOV, I., KIEVSKY, Y. & KASZPURENKO, J. M. 2007. Self-assembly of ultra-bright fluorescent silica particles. *Small*, 3, 419-423.

SOKOLOV, I. & NAIK, S. 2008. Novel fluorescent silica nanoparticles: towards ultrabright silica nanoparticles. *Small*, 4, 934-9.

SOKOLOV, I. & VOLKOV, D. O. 2010. Ultrabright fluorescent mesoporous silica particles. *Journal of Materials Chemistry*, 20, 4247-4250.

SURATWALA, T., GARDLUND, Z., DAVIDSON, K., UHLMANN, D. R., WATSON, J. & PEYGHAMBARIAN, N. 1998. Silylated coumarin dyes in sol-gel hosts. 1. Structure and environmental factors on fluorescent properties. *Chemistry of Materials*, 10, 190-198.

TAN, W., WANG, K., HE, X., ZHAO, X. J., DRAKE, T., WANG, L. & BAGWE, R. P. 2004. Bionanotechnology based on silica nanoparticles. *Med Res Rev*, 24, 621-38.

WANG, L. & TAN, W. 2006a. Multicolor FRET silica nanoparticles by single wavelength excitation. *Nano Lett*, 6, 84-8.

WANG, L. & TAN, W. H. 2006b. Multicolor FRET silica nanoparticles by single wavelength excitation. *Nano Letters*, 6, 84-88.

WANG, L., YANG, C. & TAN, W. 2005. Dual-luminophore-doped silica nanoparticles for multiplexed signaling. *Nano Lett*, 5, 37-43.

WANG, L., ZHAO, W., O'DONOGHUE, M. B. & TAN, W. 2007. Fluorescent nanoparticles for multiplexed bacteria monitoring. *Bioconjug Chem*, 18, 297-301.

YANG, H. H., QU, H. Y., LIN, P., LI, S. H., DING, M. T. & XU, J. G. 2003. Nanometer fluorescent hybrid silica particle as ultrasensitive and photostable biological labels. *Analyst*, 128, 462-466.

YANG, P., WIRNSBERGER, G., HUANG, H. C., CORDERO, S. R., MCGEHEE, M. D., SCOTT, B., DENG, T., WHITESIDES, G. M., CHMELKA, B. F., BURATTO, S. K. & STUCKY, G. D. 2000. Mirrorless lasing from mesostructured waveguides patterned by soft lithography. *Science*, 287, 465-8.

ZHAO, X. J., BAGWE, R. P. & TAN, W. H. 2004. Development of organic-dye-doped silica nanoparticles in a reverse microemulsion. *Advanced Materials*, 16, 173-+.

We claim:

1. A method for synthesizing luminescent silica particles, the method comprising the steps of:

initiating a templating synthesizing reaction configured to synthesize a plurality of nanoporous silica particles, the templating synthesizing reaction including a first template and an acidic or basic catalyst, combined with a second solution comprising water, an organosilicate or sodium silicate as a first silica precursor, and a plurality of luminophore molecules; and stirring a second silica precursor into the templating synthesizing reaction, wherein the second silica precursor is a triethoxysilane, wherein the luminophore molecules are encapsulated within a plurality of pores of said nanoporous silica particles, and further wherein said triethoxysilane prevents leakage of said luminophore molecules from said pores;

wherein the the first silica precursor comprises disodium trioxosilicate ($Na_2SiO_3 \cdot 9H_2O$), the first template comprises cetyltrimethylammonium chloride (CTAC), the catalyst comprises hydrochloric acid, the luminophore molecule comprises Rhodamine 6G (R6G), and the second silica precursor comprises ethyltriethoxysilane (ETES), wherein the molar ratio is: 0.13 $Na_2SiO_3 \cdot 9H_2O$:100 $H_2O$:X R6G:0.21 CTAC:3.9 HCl: 0.0063 ETES, where X is in the range from $3 \cdot 10^{-3}$ to $9 \cdot 10^{-3}$.

2. The method of claim 1 wherein said nanoporous silica particles have sizes ranging from 10 nm to one micron in size.

3. The method of claim 1 wherein said nanoporous silica particles have sizes greater than one micron in size.

* * * * *